United States Patent
Hedman et al.

(10) Patent No.: US 12,186,199 B2
(45) Date of Patent: Jan. 7, 2025

(54) SHIELD FOR SPINAL DEFECT

(71) Applicant: Spinal Simplicity, LLC, Overland Park, KS (US)

(72) Inventors: Thomas P. Hedman, Lexington, KY (US); Adam Rogers, Olathe, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 18/504,077

(22) Filed: Nov. 7, 2023

(65) Prior Publication Data
US 2024/0156611 A1    May 16, 2024

Related U.S. Application Data

(60) Provisional application No. 63/425,369, filed on Nov. 15, 2022.

(51) Int. Cl.
| | | |
|---|---|---|
| *A61F 2/44* | (2006.01) | |
| *A61B 17/70* | (2006.01) | |
| *A61F 2/46* | (2006.01) | |

(52) U.S. Cl.
CPC .......... *A61F 2/442* (2013.01); *A61B 17/7076* (2013.01); *A61F 2/4455* (2013.01); *A61F 2/4611* (2013.01); *A61F 2310/00389* (2013.01)

(58) Field of Classification Search
CPC ................ A61F 2/44; A61F 2002/4435; A61F 2002/445
See application file for complete search history.

(56) References Cited

U.S. PATENT DOCUMENTS

| | | |
|---|---|---|
| 5,645,597 A | 7/1997 | Krapiva |
| 6,425,919 B1 | 7/2002 | Lambrecht |
| 7,435,722 B2 | 10/2008 | Hedman |
| 7,524,333 B2 | 4/2009 | Lambrecht et al. |
| 7,972,337 B2 | 7/2011 | Boyajian et al. |
| 8,022,101 B2 | 9/2011 | Hedman |
| 8,114,082 B2 | 2/2012 | Boyajian et al. |
| 8,119,599 B2 | 2/2012 | Hedman |
| 8,153,600 B2 | 4/2012 | Hedman |
| 8,198,248 B2 | 6/2012 | Hedman |

(Continued)

FOREIGN PATENT DOCUMENTS

| | | |
|---|---|---|
| AU | 2004268628 A1 | 11/2009 |
| AU | 2010266306 A1 | 4/2014 |

(Continued)

OTHER PUBLICATIONS

PCT Patent Application PCT/US2023/36934 International Search Report and Written Opinion of the International Searching Authority issued Feb. 28, 2024.

*Primary Examiner* — Ellen C Hammond
(74) *Attorney, Agent, or Firm* — Erise IP, P.A.

(57) ABSTRACT

An intradiscal shield and an exterior shield configured to prevent re-herniation and to provide structural integrity to a spinal defect within or on a spinal disc. An insertion instrument to insert the intradiscal shield within the spinal defect and attach the intradiscal shield or exterior shield to the spinal disc. The insertion instrument having a distal tip for spraying a protein crosslinking reagent within the spinal defect. The exterior shield configured for attaching to the exterior wall of the spinal disc and blocking an exterior opening of the spinal defect.

20 Claims, 19 Drawing Sheets

(56) References Cited

U.S. PATENT DOCUMENTS

| | | |
|---|---|---|
| 8,211,938 B2 | 7/2012 | Hedman |
| 8,283,322 B2 | 10/2012 | Hedman |
| 8,361,155 B2 | 1/2013 | Lambrecht et al. |
| 8,394,146 B2 | 3/2013 | Boyajian et al. |
| 8,450,276 B2 | 5/2013 | Hedman |
| 8,454,612 B2 * | 6/2013 | Lambrecht ............. A61F 2/442 606/86 R |
| 9,039,741 B2 | 5/2015 | Lambrecht et al. |
| 9,084,772 B2 | 7/2015 | Hedman |
| 9,101,602 B2 | 8/2015 | Hedman |
| 9,192,507 B2 | 11/2015 | Hedman |
| 9,492,592 B2 | 11/2016 | Hedman |
| 9,610,106 B2 | 4/2017 | Lambrecht et al. |
| 9,918,870 B2 | 3/2018 | Hedman |
| 10,076,424 B2 | 9/2018 | Lambrecht et al. |
| 10,278,947 B2 | 5/2019 | Slusarewicz et al. |
| 10,470,804 B2 | 11/2019 | Lambrecht et al. |
| 10,980,771 B2 | 4/2021 | Slusarewicz et al. |
| 11,185,354 B2 | 11/2021 | Lambrecht et al. |
| 2003/0074075 A1 * | 4/2003 | Thomas, Jr. ............. A61B 17/70 623/908 |
| 2004/0039392 A1 * | 2/2004 | Trieu ...................... A61F 2/442 606/86 R |
| 2004/0193274 A1 * | 9/2004 | Trieu ...................... C12N 5/0667 435/377 |
| 2005/0119754 A1 * | 6/2005 | Trieu ...................... A61F 2/4601 623/17.11 |
| 2007/0244562 A1 * | 10/2007 | Conner .................. A61F 2/4684 623/23.75 |
| 2008/0071281 A1 | 3/2008 | Wilson et al. |
| 2009/0138084 A1 * | 5/2009 | Conner ............. A61B 17/1671 623/17.11 |
| 2010/0256766 A1 | 10/2010 | Hibri et al. |
| 2011/0118844 A1 * | 5/2011 | Lambrecht ............ A61F 2/4657 623/17.16 |
| 2014/0180415 A1 | 6/2014 | Koss |
| 2019/0133777 A1 | 5/2019 | Müller et al. |
| 2019/0274844 A1 * | 9/2019 | Seifert .................... A61F 2/442 |

FOREIGN PATENT DOCUMENTS

| | | |
|---|---|---|
| CA | 2458821 C | 3/2003 |
| CA | 2536415 A1 | 3/2005 |
| CA | 2770153 A1 | 1/2011 |
| TW | 200526203 A | 8/2005 |
| WO | 2007011994 A2 | 1/2007 |

* cited by examiner

SHIELD FOR SPINAL DEFECT

RELATED APPLICATIONS

This non-provisional patent application claims prior benefit, with regard to all subject matter, of U.S. Provisional Patent Application No. 63/425,369, filed Nov. 15, 2022, and entitled "SHIELD FOR SURGICAL DEFECT". The above-identified application is hereby incorporated by reference in its entirety.

This application shares certain subject matter in common with earlier-filed U.S. patent application Ser. No. 13/940,868, filed Jul. 12, 2013, entitled "INTERSPINOUS PROCESS IMPLANT HAVING DEPLOYABLE ANCHOR BLADES"; now U.S. Pat. No. 9,757,164. This patent application shares certain subject matter in common with earlier-filed U.S. patent application Ser. No. 15/159,189, filed May 19, 2016, entitled "INTERSPINOUS PROCESS IMPLANT HAVING A BODY WITH A REMOVABLE END "ORTION"; now U.S. Pat. No. 9,861,399. This patent application shares certain subject matter in common with earlier-filed U.S. patent application Ser. No. 16/998,171, filed Aug. 20, 2020, entitled "INTERSPINOUS PROCESS IMPLANT"; now U.S. Pat. No. 11,311,388. This patent application shares certain subject matter in common with earlier-filed U.S. patent application Ser. No. 17/677,677, filed Feb. 22, 2022, entitled "INTERSPINOUS PROCESS IMPLANT"; now U.S. Pat. No. 11,534,310. This patent application shares certain subject matter in common with earlier-filed U.S. patent application Ser. No. 14/560,006, filed Dec. 4, 2014, entitled "INTERSPINOUS PROCESS IMPLANT AND FUSION CAGE SPACER"; now U.S. Pat. No. 9,314,276. This patent application shares certain subject matter in common with earlier-filed U.S. patent application Ser. No. 15/085,687, filed Mar. 30, 2016, entitled "INTERSPINOUS PROCESS IMPLANT AND FUSION CAGE SPACER"; now U.S. Pat. No. 9,907,581. The above-referenced patent applications are hereby incorporated by reference in their entirety into the present application.

BACKGROUND

1. Field

Embodiments of the present disclosure generally relate to systems, devices, and methods for spinal procedures. More specifically, embodiments of the present disclosure relate to systems, devices, and methods for stabilizing a spinal defect in a spinal disc.

2. Related Art

Post-discectomy surgeries or other decompression surgeries present post-procedure problems. There is a high likelihood of re-herniation of nucleus material out of the spinal disc that has remained following the procedure. When following a fenestration discectomy where nucleus material is surgically removed from the inside of the disc, this re-herniation typically occurs at the site of the surgery due to damage to and removal of annulus tissue at the surgical site. For example, the damage to and removal of annulus tissue may create a spinal defect and the re-herniation may occur through the spinal defect left after the surgery. In the case of a less aggressive, minimally invasive "micro-discectomy" procedure, only nucleus material that was herniated out of the disc is surgically severed, clipped, or otherwise removed, leaving behind a defect related to the original disc herniation (e.g., fissure, tear). Re-herniation can also occur in less aggressive discectomies as well through the same disc tear or fissure involved with the prior disc herniation. Herniated material can press on nerve roots and cause radiating pain in the patient.

Following the fenestration discectomy procedure, there are regularly adverse effects on the mechanical properties of the spinal disc. This includes destabilization of the spinal disc due to disruption of a portion of the outer annular region of the spinal disc, which is a result of the decompression or discectomy procedure in addition to the damage resulting from the prior disc herniation. Additionally, fissures or tears from an original disc herniation remaining after a micro-discectomy procedure may also affect the stability of the spinal joint, for example, at the spinal disc. Devices exist for preventing re-herniation. However, existing devices do not provide joint and disc stabilization through the injection or release of protein crosslinker into the spinal defect. Accordingly, there is a need for mechanical stabilization of the spinal disc following these procedures so as to preclude re-herniation and mechanical degradation.

SUMMARY

Embodiments of the present disclosure solve the above-mentioned problems by providing a device, system, and method for providing structural and mechanical integrity to a spinal disc having a spinal defect. For example, the spinal defect may remain following surgery. The spinal defect may occur from an original disc herniation.

In some embodiments, the techniques described herein relate to an intradiscal shield configured to provide structural integrity to a spinal disc having a spinal defect, the intradiscal shield comprising: an outer barrier defining an inner portion, wherein the inner portion defines a bore; a first side configured to face a central cavity of the spinal disc; a second side, opposite the first side, and configured to face outwardly from the central cavity, wherein the second side includes an instrument engagement member, wherein the bore extends through the inner portion and the instrument engagement member; and one or more anchors extending from the outer barrier and configured to maintain a position of the intradiscal shield within the spinal defect, wherein the bore is configured to transition between an open configuration and a closed configuration, wherein, in the open configuration, the bore provides an opening for spraying a protein crosslinking reagent therethrough.

In some embodiments, the techniques described herein relate to an intradiscal shield, wherein the bore biases into the closed configuration, wherein the spinal defect is a surgical defect.

In some embodiments, the techniques described herein relate to an intradiscal shield, wherein the bore is configured to transition into the open configuration upon interaction with an insertion instrument, wherein, in the open configuration, the bore receives the protein crosslinking reagent to thereby release the protein crosslinking reagent into the central cavity of the spinal defect, such that the protein crosslinking reagent stabilizes the spinal disc.

In some embodiments, the techniques described herein relate to an intradiscal shield, wherein the one or more anchors are angled acutely towards the second side, wherein the one or more anchors are configured to insert into a perimeter tissue of the spinal defect to maintain the position of the intradiscal shield within the spinal defect.

In some embodiments, the techniques described herein relate to an intradiscal shield, wherein the instrument engagement member includes one or more stabilizers, wherein the one or more stabilizers are configured to stabilize the intradiscal shield.

In some embodiments, the techniques described herein relate to an intradiscal shield, wherein one or more of the outer barrier or the first side include a coating of a degradable polymer having a protein crosslinker contained therein.

In some embodiments, the techniques described herein relate to a surgical system configured to insert an intradiscal shield into a spinal defect of a spinal disc, the surgical system comprising: the intradiscal shield, comprising: an outer barrier; an inner portion defined within the outer barrier, the inner portion having a first side configured to face inwardly within the spinal defect and a second side configured to face outwardly from the spinal defect; an instrument engagement member disposed on the second side; and a bore defined by the inner portion and the instrument engagement member, the bore configured to transition between an open configuration and a closed configuration; and an insertion instrument, comprising: a luer lock disposed at a proximal end; a shaft extending distally from the luer lock and defining a hollow tube therein; a distal tip configured to transiently attach to the instrument engagement member of the intradiscal shield; and a spraying end included in the distal tip, wherein the bore of the intradiscal shield is configured to receive the spraying end of the insertion instrument to thereby maintain the bore in the open configuration, wherein the spraying end sprays a protein crosslinker through the bore when the bore is in the open configuration.

In some embodiments, the techniques described herein relate to a surgical system, wherein the spraying end sprays the protein crosslinker through the bore into the spinal defect when the bore is in the open configuration, to thereby stabilize the spinal disc having the spinal defect.

In some embodiments, the techniques described herein relate to a surgical system, the intradiscal shield further including: one or more anchors disposed on the outer barrier and configured to maintain a position of the intradiscal shield within the spinal defect.

In some embodiments, the techniques described herein relate to a surgical system, wherein proximal translation of the insertion instrument while attached to the intradiscal shield is configured to seat the one or more anchors of the intradiscal shield into the spinal defect.

In some embodiments, the techniques described herein relate to a surgical system, the insertion instrument further including: a shield bore opening device received in the hollow tube of the shaft and configured to transition the bore of the intradiscal shield between the open configuration and the closed configuration, wherein the luer lock is configured to attach to a syringe, the syringe retaining a liquid including the protein crosslinker configured for spraying through the bore via the spraying end.

In some embodiments, the techniques described herein relate to a surgical system, wherein the distal tip comprises one or more extensions, wherein the one or more extensions are configured to engage the second side of the inner portion of the intradiscal shield to thereby stabilize a connection between the intradiscal shield and the insertion instrument.

In some embodiments, the techniques described herein relate to a surgical system, wherein the instrument engagement member includes one or more stabilizers, wherein the one or more stabilizers are configured to stabilize the intradiscal shield.

In some embodiments, the techniques described herein relate to a surgical system, further including: an exterior shield having an attachment mechanism and configured to attach to an exterior wall of the spinal disc over the spinal defect, wherein the attachment mechanism is selected from a group consisting of: one or more sutures, one or more sutures coated with a degradable polymer containing a protein crosslinker, barbed tacks, one or more barbed tacks coated with a degradable polymer containing a protein crosslinker, and an adhesive material.

In some embodiments, the techniques described herein relate to a surgical system, the exterior shield further including: one or more sharp protrusions extending from the exterior shield, the one or more sharp protrusions configured to engage a vertebra juxtaposed to the spinal disc.

In some embodiments, the techniques described herein relate to a method for providing structural integrity to a spinal disc having a spinal defect, the method comprising: attaching an intradiscal shield to a distal tip of an insertion instrument; inserting the intradiscal shield into the spinal defect, the intradiscal shield comprising: an outer barrier defining an inner portion and one or more anchors disposed in the outer barrier and extending outwardly therefrom, wherein the inner portion includes a first side facing a central cavity of the spinal disc and a second side facing outwardly from the central cavity, wherein the inner portion defines a bore; seating the one or more anchors into a perimeter tissue of the spinal defect, the perimeter tissue defining the spinal defect; releasing a protein crosslinking reagent into the central cavity and the spinal defect, wherein the distal tip of the insertion instrument releases the protein crosslinking reagent through the bore of the intradiscal shield; and detaching the intradiscal shield from the distal tip.

In some embodiments, the techniques described herein relate to a method, further including: coating one or more of the outer barrier or the first side with the protein crosslinking reagent prior to inserting the intradiscal shield into the spinal defect.

In some embodiments, the techniques described herein relate to a method, further including: rotating a shield bore opening device included in the insertion instrument to transition the bore from a closed configuration to an open configuration.

In some embodiments the techniques described herein relate to a method, further including: attaching an exterior shield to the spinal disc, wherein the exterior shield covers an exterior opening of the spinal defect.

In some embodiments, the techniques described herein relate to a method, wherein attaching the exterior shield to the spinal disc includes suturing the exterior shield to the spinal disc via a plurality of sutures, the plurality of sutures being coated in the protein crosslinking reagent.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present disclosure will be apparent from the following detailed description of the embodiments and the accompanying drawing figures.

BRIEF DESCRIPTION OF THE DRAWING FIGURES

Embodiments of the present disclosure are described in detail below with reference to the attached drawing figures, wherein.

Figure 1:
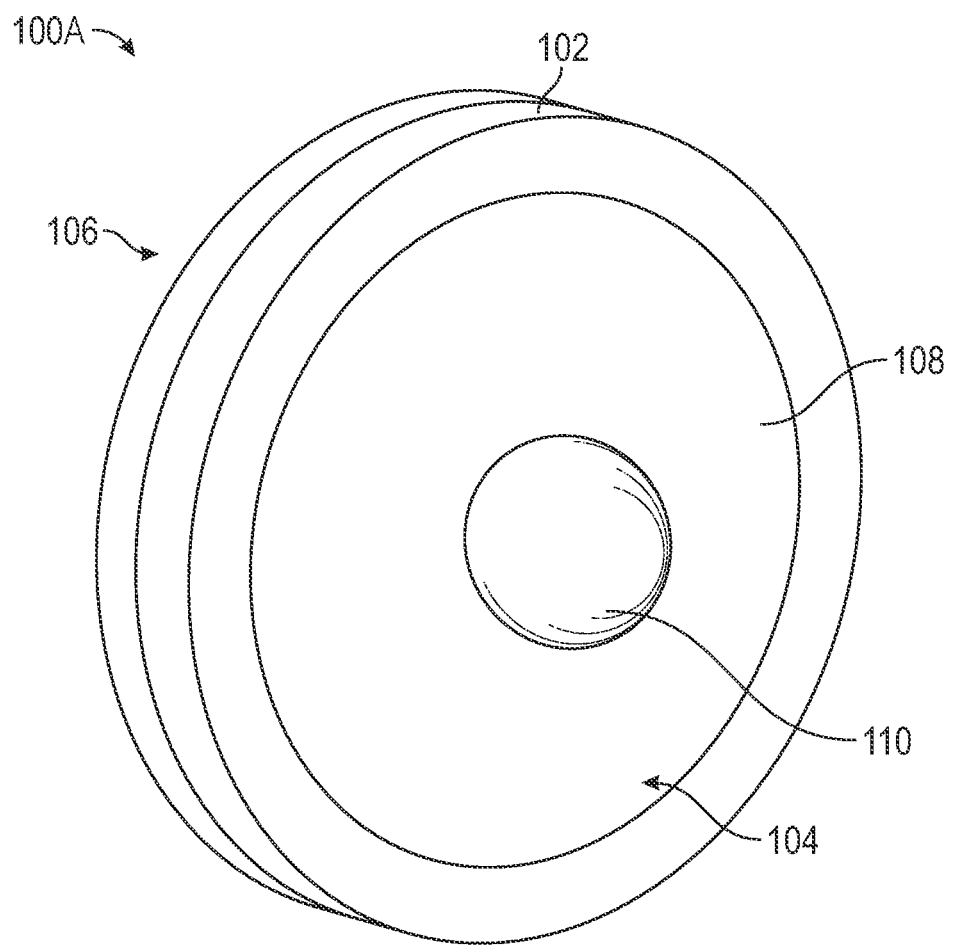
FIG. 1 depicts a perspective view of some embodiments of an intradiscal shield.

The drawing figures do not limit the present disclosure to the specific embodiments disclosed and described herein. The drawings are not necessarily to scale, emphasis instead being placed upon clearly illustrating the principles of the present disclosure.

DETAILED DESCRIPTION

The subject matter of the present disclosure is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be understood by one skilled in the art and are intended to be captured within the scope of the present disclosure. Terms should not be interpreted as implying any particular ordering of various steps described unless the order of individual steps is explicitly described.

The following detailed description references the accompanying drawings that illustrate specific embodiments in which the present disclosure can be practiced. The embodiments are intended to describe aspects of the present disclosure in sufficient detail to enable those skilled in the art to practice the present disclosure. Other embodiments can be utilized, and changes can be made without departing from the scope of the present disclosure. The following detailed description is, therefore, not to be taken in a limiting sense. The scope of the present disclosure is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

In this description, references to "spinal defect" or "defect" may refer to any cut, clip, tear, fissure, gash, tunnel, hole, bore, surgical defect, etc. created through a surgical procedure, a spinal injury, treatment of a spinal injury, or degradation over time. For example, a spinal defect may involve a fissure from herniation of a spinal disc, a fissure created through a micro-discectomy, or a surgical defect created through a fenestration discectomy. Therefore, in some instances, references to "spinal defect" or "defect" may include defects created by surgery, defects that may require surgery, and defects formed through injury or degradation over time.

FIGS. 1, 2A-3, 9A-9B, and 10A-10B depict some embodiments of an intradiscal shield 100A, 100B, 100C, 100D. For example, FIG. 1 depicts some embodiments of an intradiscal shield 100A. In some embodiments, intradiscal shield 100A, 100B, 100D includes outer barrier 102 defining an inner portion 104, the inner portion 104 having a first side 106 and a second side 108 with an instrument engagement member 110 extending therefrom. Though not shown in FIGS. 9A-9B, intradiscal shield 100C may include outer barrier 102 defining an inner portion 104, the inner portion 104 having a first side 106 and a second side 108 with an instrument engagement member 110. Intradiscal shield 100A, 100B, 100C, 100D is configured to be inserted into, and remain within, a spinal defect (e.g., spinal defect 302A depicted in FIG. 5, FIG. 9A, FIG. 10A) of a spinal disc (e.g., spinal disc 300 depicted in FIG. 5, FIG. 9A, FIG. 10A). A surgical defect is an example of a spinal defect 302A. As described above, following fenestration discectomy surgery on a spinal disc, a resultant spinal defect (e.g., surgical defect) is left behind. Typically, in a fenestration discectomy procedure, the central nucleus tissue of the spinal disc is partially or mostly removed, thereby leaving behind a central cavity within the central region of the spinal disc along with a spinal defect left through the inner and outer annulus tissue. The spinal defect can thus lead to an increased likelihood of re-herniation (i.e., a portion of any leftover central nucleus tissue, such as remaining tissue in the central cavity 308 depicted in FIG. 8, may leak out of the spinal defect). Furthermore, the spinal defect causes mechanical destabilization of the spinal disc, which can exacerbate some symptoms experienced by the patient, such as back pain at the site of the spinal joint. Accordingly, placement of intradiscal shield 100A, 100B, 100C, 100D within the spinal defect (e.g., surgical defect) may preclude or prevent re-herniation as well as provide mechanical stabilization of the spinal disc following a surgical procedure (e.g., discectomy).

Figure 7:
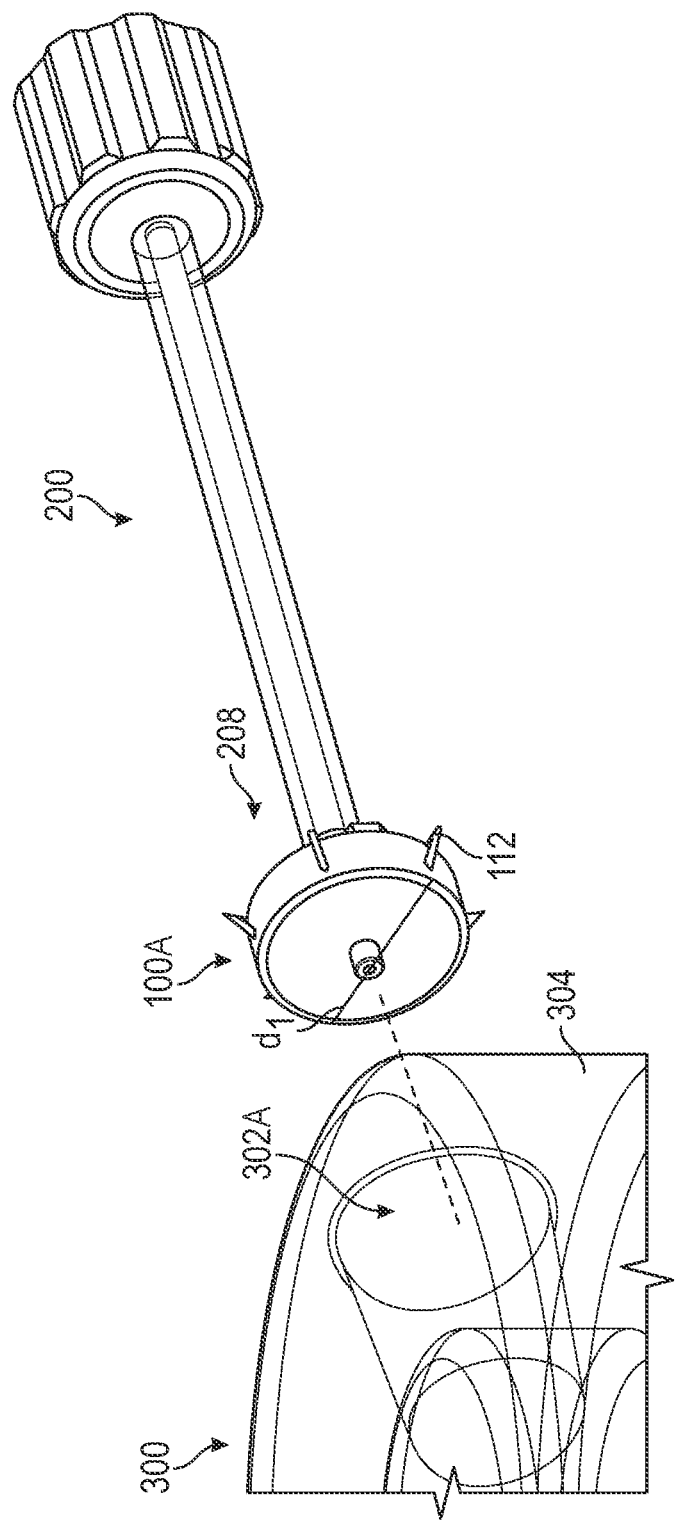
FIG. 7 illustrates some embodiments of the surgical system with the intradiscal shield attached to the insertion instrument.

In some embodiments, as illustrated in FIG. 1, outer barrier 102 defines an inner portion 104. Outer barrier 102 may be configured to press against the perimeter tissue of the spinal defect (e.g., perimeter tissue 306 and spinal defect 302A depicted in FIG. 5). As is clear from the depiction, perimeter tissue 306 is the tissue within spinal disc 300 defining spinal defect 302A. Outer barrier 102 may be configured in any desired shape and/or size so as to provide a complete seal between outer barrier 102 and the perimeter tissue 306. For example, in some embodiments, outer barrier 102 may comprise a round, oblong, square, rectangular, or any other shape that the perimeter tissue 306 of spinal defect 302A may comprise. The shape of spinal defect 302A may be determined based on the tool, direction, etc. of the surgery that is performed on spinal disc 300. As such, intradiscal shield 100A, 100B, 100C, 100D and outer barrier 102 may be designed or otherwise configured based on the anticipated size and shape of spinal defect 302A. In some embodiments, the angle of outer barrier 102 may be tapered between first side 106 and second side 108. For example, the diameter/width/size of outer barrier 102 may be smaller at first side 106 than the diameter/width/size of outer barrier 102 at second side 108. For example, first side 106 may define a first diameter $d_1$ (otherwise referred to as width herein, shown in FIG. 2B) and second side 108 may define a second diameter $d_2$ (as shown in FIG. 7). The second diameter $d_2$ may be greater than the first diameter $d_1$. For example, first diameter $d_1$ may be within a range of about 0.5 mm to about 6 mm, such as between about 2 mm to about 4 mm, while second diameter $d_2$ may be within a range of about 5 mm to about 12 mm, such as between about 6 mm to about 10 mm. "About" means +/−0.5 mm or +/−5% deviation. Such a configuration may allow for enhanced sealing between outer barrier 102 and spinal defect 302A.

In some embodiments, the tapering of the angle of outer barrier 102 may create a gradient of widths between the first side and the second side. In these embodiments, diameter $d_1$ may be a first minimum width of first side 106, with the first minimum width being within a range of about 0.5 mm to about 6 mm, such as between about 2 mm to about 4 mm. The second diameter $d_2$ may be a second minimum width of second side 108, with the second minimum width being within the range of about 5 mm to about 12 mm, such as between about 6 mm to about 10 mm. Thus, in some embodiments, the first minimum width of the first side 106 may be less than the second minimum width of the second side 108. For example, first side 106 may have a first diameter $d_1$/minimum width of about 4 mm and second side 108 may have a second diameter $d_2$/minimum width of about 8 mm. Yet further, in some embodiments, outer barrier 102 may comprise a rim (not shown) on the proximal side (i.e., second side 108) that has a larger diameter/size/width than the opening of spinal defect 302A. Accordingly, the rim may contact exterior wall 304 of spinal disc 300 and help prevent re-herniation. In these embodiments, the rim may be additionally attached to exterior wall 304 via an adhesive (e.g., fibrin glue, cyanoacrylate, etc.), amine groups that interact with protein crosslinking reagents disposed on exterior wall 304, and/or sewing of the rim to exterior wall 304, and/or tacking of the rim to exterior wall 304, and/or tacking to exterior of vertebral bone above or below spinal disc. In embodiments in which the rim is sewn to exterior wall 304, a suture delivery device (not shown) may be used. For descriptive purposes, the suture delivery device may enter spinal disc 300 through the rim or lateral edge of outer barrier 102. The suture delivery device may then arc across the interior annulus tissue and exit the spinal disc 300 through the rim or lateral edge of outer barrier 102 on the opposite side of the rim or adjacent to the entry point. In some embodiments, the needle used to insert sutures may be curved and shaped appropriately to enter spinal disc 300 through the rim or lateral edge of outer barrier 102 on one side of intradiscal shield 100A, 100B, 100D, exit the spinal disc 300, and go through the rim or lateral edge of outer barrier 102 on the opposite or adjacent side of the rim to be secured by a knot.

In some embodiments, outer barrier 102 may be made of a partially elastic material so as to allow for some deformation while inserting/placing intradiscal shield 100A, 100B, 100C, 100D within spinal defect 302A. For example, outer barrier 102 may be made of a polymer or degradable polymer. Furthermore, inner portion 104 may similarly be partially elastic/flexible so as to allow intradiscal shield 100A, 100B, 100C, 100D to partially deform during insertion/placement of intradiscal shield 100A within spinal defect 302A. For example, when inserting intradiscal shield 100A, 100B, 100C, 100D into spinal defect 302A, intradiscal shield 100A may become partially concave while being pushed into spinal defect 302A. Such concavity may be due to the diameter/size of intradiscal shield 100A, 100B, 100C, 100D and outer barrier 102 being slightly larger than the diameter/size of spinal defect 302A. As will be discussed in greater detail below, upon pulling/seating intradiscal shield 100A, 100B, 100C, 100D within spinal defect 302A, the concavity may decrease such that outer barrier 102 forms a seal along the perimeter tissue 306 of spinal defect 302A.

In some embodiments, to aid in placement and seating of intradiscal shield 100A, 100B, 100C, 100D within spinal defect 302A, outer barrier 102 may be coated with a biocompatible adhesive. For example, outer barrier 102 may be coated in fibrin glue, cyanoacrylate adhesive, or any other biocompatible adhesive material. Alternatively, or additionally, in some embodiments, outer barrier 102 may be coated with amine groups (i.e., amine functionalized polymers). Further, a protein crosslinker embedded in a degradable polymer may be applied to the perimeter tissue 306, such that upon placement of intradiscal shield 100A, 100B, 100C, 100D within spinal defect 302A, the amine group coating disposed or located on outer barrier 102 binds with the protein crosslinker on the perimeter tissue 306 and aids in placement/seating of intradiscal shield 100A, 100B, 100C, 100D. Alternatively, a liquid comprising a protein crosslinking reagent is applied to the perimeter tissue 306 by spraying or brushing, such that upon placement of intradiscal shield 100A, 100B, 100C, 100D within spinal defect 302A, the amine group coating disposed or located on outer barrier 102 binds with the protein crosslinker on the perimeter tissue 306 and aids in placement/seating of intradiscal shield 100A, 100B, 100C, 100D. Alternatively, or additionally, in some embodiments, a coating on outer barrier 102 may contain amine groups (i.e., amine functionalized polymers) in some regions and a protein crosslinker embedded in a degradable polymer in other regions. Alternatively, or additionally, in some embodiments, intradiscal shield 100A, 100B, 100C, 100D may be sewn into spinal defect 302A. For example, sutures may be used to attach outer barrier 102 to the perimeter tissue 306. The sutures may be coated with a degradable polymer containing a protein crosslinking reagent therein, such as those disclosed in U.S. Pat. No. 10,278,947, which is hereby incorporated by reference in its entirety. In embodiments in which the outer barrier 102 is sewn to the perimeter tissue 306, a suture delivery device (not shown) may be used. For descriptive purposes, the suture delivery device may enter spinal disc 300 through outer barrier 102 or edge of outer barrier 102. The suture delivery device may then arc across the interior annulus surrounding the spinal defect 302A and exit near where it entered the outer barrier 102 to be secured to the tail of the suture. In some embodiments, the needle used to insert sutures may be curved and shaped appropriately to enter intradiscal shield 100A, 100B, 100C, 100D or outer barrier 102 on one side of intradiscal shield 100A, 100B, 100C, 100D, exit on an opposing side of intradiscal shield 100A, 100B, 100C, 100D, and arc through adjacent tissue of spinal disc 300, and exit the adjacent tissue of spinal disc 300 to be secured to the tail end of the suture.

Figure 2B:
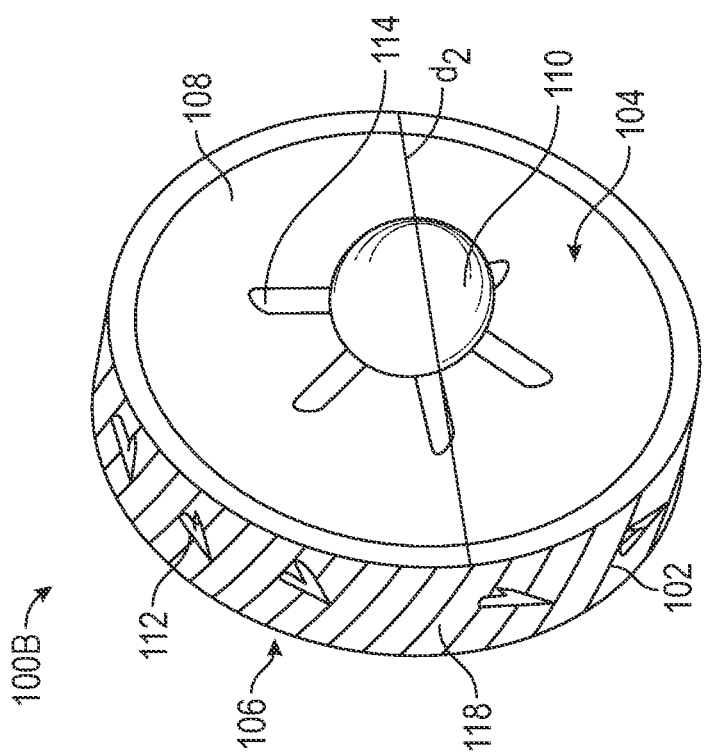
FIG. 2B depicts a perspective view of some embodiments of the intradiscal shield.
Figure 2A:
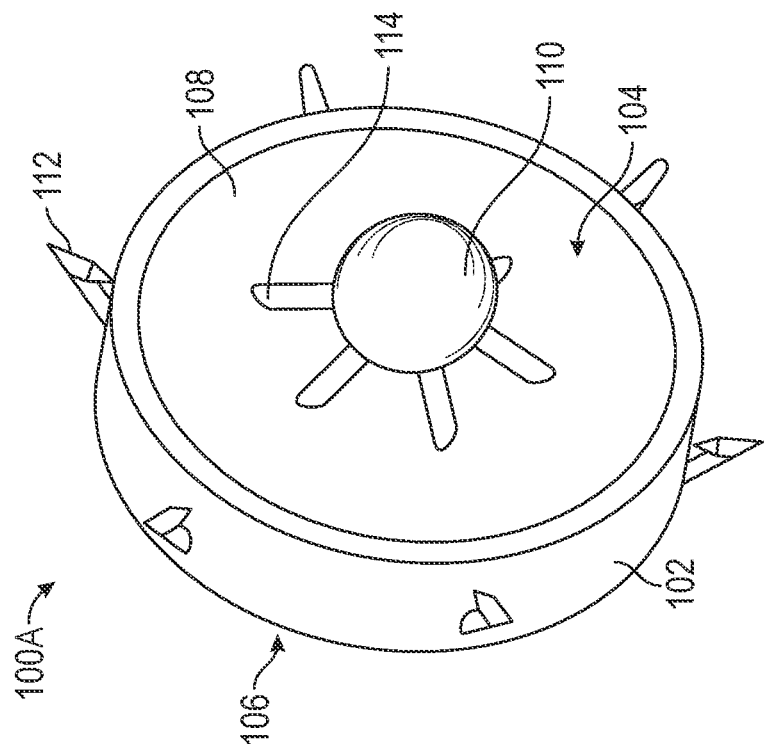
FIG. 2A depicts a perspective view of some embodiments of the intradiscal shield.

As illustrated in FIGS. 1 and 2A-2B, intradiscal shield 100A, 100B may include an instrument engagement member 110 (also referred to as an instrument engagement portion). Intradiscal shield 100C, 100D may include an instrument engagement member 110 (not shown). As discussed above and depicted, instrument engagement member 110 may extend from second side 108 of inner portion 104. In some embodiments, and as will be discussed in greater detail below, instrument engagement member 110 may be configured to interact, engage, or otherwise transiently attach to an insertion instrument (e.g., insertion instrument 200 depicted in FIG. 4). As such, instrument engagement member 110 allows for an instrument, such as insertion instrument 200, to insert intradiscal shield 100A, 100B, 100C, 100D into spinal defect 302A. Instrument engagement member 110 may comprise any shape that allows for partial gripping or engagement with insertion instrument 200. For example, instrument engagement member 110 may comprise a sphere, knob, hook, ring, or any other shape allowing attachment to insertion instrument 200.

Figure 11:
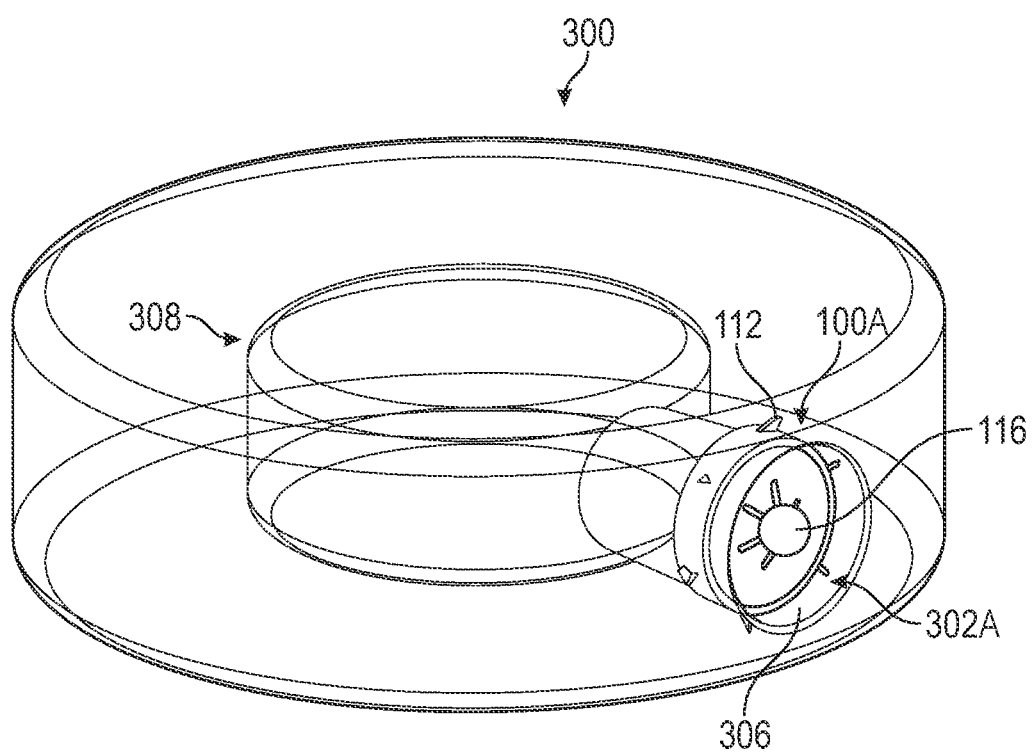
FIG. 11 illustrates some embodiments of the intradiscal shield within the spinal defect of the spinal disc.

In some embodiments, first side 106 is configured to face inwardly (i.e., towards the center of spinal disc 300, such as, e.g., toward central cavity 308) when inserted into spinal defect 302A while second side 108 is configured to face outwardly (i.e., away from the center of spinal disc 300, such as, e.g., away from central cavity 308) when inserted into spinal defect 302A (e.g., see FIG. 11). In some embodiments, first side 106 may include a mechanically advantageous compound or material that aids in re-stabilization of spinal disc 300 following creation of spinal defect 302A. In some embodiments, intradiscal shield 100A, 100B, 100C, 100D may be made of any medical-grade materials such as medical-grade plastics, polycarbonates (PC), polypropylene (PP), polyethylene (PE), polyvinyl chloride (PVC), acrylonitrile butadiene styrene (ABS), polystyrene (PS), polyethylene terephthalate glycol (PETG), polymethyl methacrylate (PMMA), polyether ether ketone (PEEK), polymers, bioabsorbable material, polymers, metals, stainless steel, copper, titanium, cobalt chrome, aluminum, magnesium, additive manufactured materials, titanium-based alloys, cobalt-based alloys, nylon, thermoplastic polyurethane (TPU), polyphenylsulfone (PPSU), polyamide-imide (PAI), or combinations thereof, as well as any other suitable medical-grade materials or constituents thereof. For example, in some embodiments, first side 106 may be coated with a degradable polymer containing a protein crosslinker, such as genipin. Further, a portion or all of first side 106 may be made of a polymer, and potentially a degradable polymer, having the protein crosslinker embedded therein. Such a protein crosslinker may aid in restabilizing the spinal joint following surgery. Embodiments are also contemplated in which a portion or all of intradiscal shield 100A, 100B, 100C, 100D may be manufactured using additive manufacturing.

Figure 3:
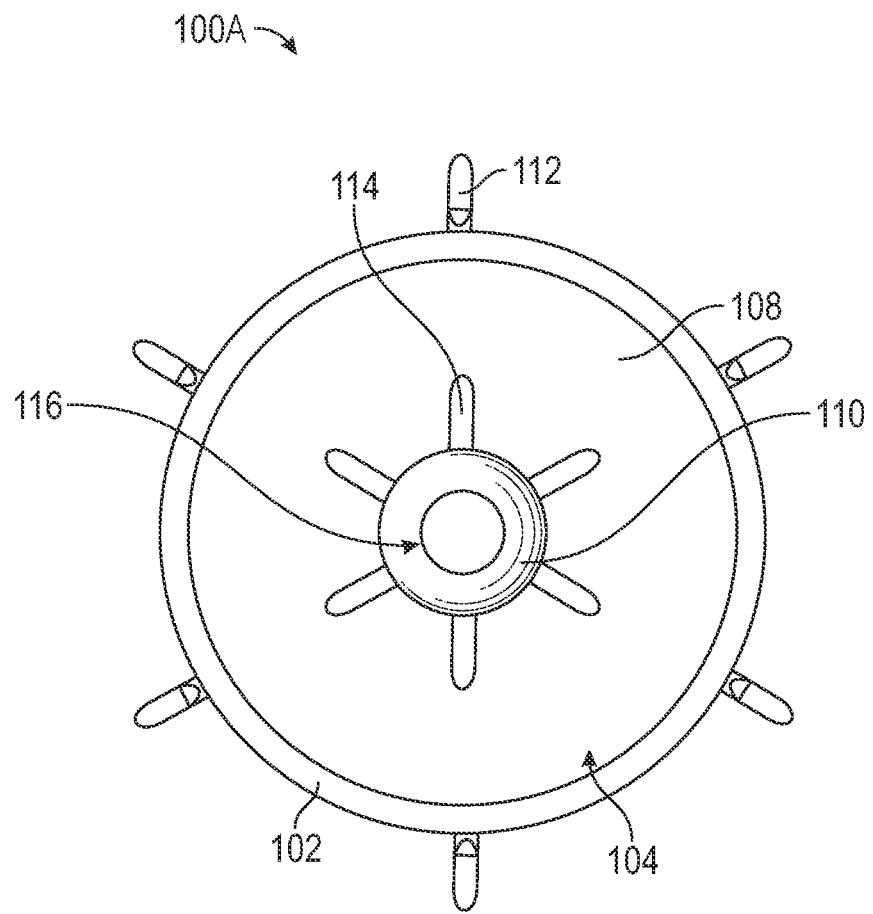
FIG. 3 depicts a front view of some embodiments of the intradiscal shield, such as those shown in FIG. 2A.

FIG. 2A illustrates a perspective view of some embodiments of intradiscal shield 100A. FIG. 2B illustrates a perspective view of some embodiments of intradiscal shield 100B. FIG. 3 illustrates a frontal view of some embodiments of intradiscal shield 100A. Accordingly, FIGS. 2A-3 are best viewed together for the following description.

In some embodiments, intradiscal shield 100A, 100B may include one or more anchors 112 extending outwardly and configured to engage the perimeter tissue 306 when placed in spinal defect 302A. For example, one or more anchors 112 may be ratchet-shaped edges, projections, clips, or barbed pins that engage the surrounding tissue (e.g., perimeter tissue 306) when intradiscal shield 100A is seated into spinal defect 302A. In some embodiments, anchors 112 may extend outwards from outer barrier 102 and contain sharp edges facing towards second side 108. Further, anchors 112 may be angled acutely towards second side 108 such that when intradiscal shield 100A, 100B is being inserted into spinal defect 302A (i.e., translated in the distal direction, towards the central cavity 308), anchors 112 will bend inwardly toward outer barrier 102 and not engage with the perimeter tissue 306. Upon insertion of intradiscal shield 100A into spinal defect 302A, intradiscal shield 100A may be seated into spinal defect 302A via pulling, or outward, proximal biasing, of intradiscal shield 100A using insertion instrument 200 (see arrow in FIG. 8). Such a movement may, in some embodiments, cause insertion of anchors 112 within the perimeter tissue 306. By inserting anchors 112 into the perimeter tissue 306 in this manner, intradiscal shield 100A may resist pressure coming from the disc central region and thus preclude the likelihood of shield expulsion or re-herniation following surgery.

In some embodiments, instrument engagement member 110 may include stabilizers 114 that aid in keeping instrument engagement member 110 attached to intradiscal shield 100A, 100B, 100C, 100D and aid in keeping intradiscal shield 100A, 100B, 100D perpendicular to the long axis of insertion instrument 200. In some embodiments, stabilizers 114 may extend through inner portion 104 and be connected to anchors 112. Such a configuration may enhance the stability of intradiscal shield 100A, 100B, 100C, 100D as it remains within spinal defect 302A and experiences different pressures exerted on the spinal joint and spinal disc 300.

In some embodiments, and as will be discussed in greater detail below, instrument engagement member 110 and inner portion 104 may include bore 116 extending therethrough. In these embodiments, bore 116 may be configured to transition between an open configuration and a closed configuration. For example, bore 116 may be naturally biased towards a closed configuration, but may transition to an open configuration by interaction with a portion of insertion instrument 200. Bore 116 may be configured to allow certain factors, liquids, materials, or similar to be released therethrough and into the central compartment (i.e., central cavity 308) of spinal disc 300 (e.g., see FIG. 8). For example, bore 116 may receive a portion of insertion instrument 200 when in the opened configuration to thereby pass a protein cross-linking reagent through the spinal defect into the central cavity 308.

FIG. 2B illustrates some embodiments of intradiscal shield 100B. In some embodiments, outer barrier 102 of intradiscal shield 100B, 100C may comprise threads 118. Rotation of intradiscal shield 100B, 100C in a first direction may move the intradiscal shield 100B into spinal defect 302A. For example, rotation of intradiscal shield 100B, 100C in a first direction may translate the intradiscal shield 100B, 100C into spinal defect 302A. Threads 118 may engage with perimeter tissue 306 of spinal defect 302A via rotation of intradiscal shield 100B, 100C in a first direction. In some embodiments, at least a portion of threads 118 may comprise anchors 112 defined on an outer portion of the portion of threads 118. The anchors 112 extending from the threads may align with the circumference of outer barrier 102 of intradiscal shield 100B, such that the anchors 112 extend from the outer portion of the portion of threads 118 to the diameter of outer barrier 102. Rotating the intradiscal shield 100B in a second direction may engage the anchors 112 with the spinal defect 302AA, thereby seating the intradiscal shield 100B into spinal defect 302A. The intradiscal shield 100B may be seated into spinal defect 302A via rotation of intradiscal shield 100B in a second direction using insertion instrument 200. For example, rotating the intradiscal shield 100B in a second direction may engage anchors 112 into perimeter tissue 306. The second rotation direction may be opposite the first rotation direction. In such an embodiment, rotational movement in a first direction (e.g., clockwise rotation) translates the intradiscal shield 100B into spinal defect 302A to thereby insert the intradiscal shield 100B into spinal defect 302A, while rotational movement in a second direction (e.g., counterclockwise rotation) engages anchors 112 with perimeter tissue 306 to maintain the position of the intradiscal shield 100B within spinal defect 302A.

The anchors 112 may be ratchet-shaped edges, projections, clips, or barbed pins that engage the surrounding tissue (e.g., perimeter tissue 306) when intradiscal shield 100B is seated into spinal defect 302A. In some embodiments, anchors 112 may contain sharp edges facing towards second side 108. Further, anchors 112 may be angled acutely towards second side 108 such that when intradiscal shield 100B is being inserted into spinal defect 302A (i.e., translated in the distal direction via rotation in a first direction, towards the central cavity 308), anchors 112 will not engage with the perimeter tissue 306. Upon insertion of intradiscal shield 100B into spinal defect 302A, intradiscal shield 100B may be seated into spinal defect 302A via rotation of the shield 100B in a second direction, to thereby engage the anchors 112 with the spinal defect 302A.

Embodiments are contemplated in which threads 118 of intradiscal shield 100B, 100C may provide an interference fit between the outer barrier 102 and perimeter tissue 306 of spinal defect 302A to secure intradiscal shield 100B, 100C into spinal defect 302A. Intradiscal shield 100B, 100C may be inserted into spinal defect 302A through rotational motion of an insertion instrument 200 (see, e.g., insertion instrument of FIG. 6). The insertion instrument 200 may engage with the instrument engagement member 110 of intradiscal shield 100B (see FIG. 2B), 100C (not shown), such that rotation of the insertion instrument 200 causes the threads 118 of intradiscal shield 100B, 100C to rotate and engage with perimeter tissue 306 of spinal defect 302A. The rotation of threads 118 causes intradiscal shield 100B, 100C to translate distally into spinal defect 302A. In some embodiments of intradiscal shield 100B, 100C, instrument engagement member 110 and inner portion 104 may include bore 116 (not shown in FIG. 2B, not shown in FIGS. 9A-9B) extending therethrough that may transition to an open configuration by interaction with a portion of insertion instrument 200, as further discussed below. In these embodiments, bore 116 may be configured to transition between an open configuration and a closed configuration. Engagement of insertion instrument with instrument engagement member 110 may cause bore 116 of intradiscal shield 100B, 100C to transition to an open configuration and receive at least a portion of insertion instrument 200.

In some embodiments, intradiscal shield 100C, 100D comprises a first deployable anchor 120A and a second deployable anchor 120B (also referred to as a first wing and a second wing) (see, e.g., FIGS. 9A-10B). Further, in some embodiments, the first deployable anchor 120A and the second deployable anchor 120B may be stored within substantially rectangular windows 122A, 122B defined by the intradiscal shield 100C (see FIG. 9A). Embodiments are also considered in which deployable anchors 120A, 120B are stored within one substantially rectangular window. In some embodiments, deployable anchors 120A, 120B may be stored within at least a portion of outer barrier 102 of intradiscal shield 100D (see FIG. 10A). Alternatively, or additionally, in some embodiments, the first deployable anchor 120A and the second deployable anchor 120B may be flush or almost flush with the circumference of outer barrier 102 of intradiscal shield 100D, as shown in FIG. 10A.

In some embodiments, intradiscal shield 100C, 100D may comprise more than two deployable anchors. For example, intradiscal shield 100C, 100D comprises a first pair of deployable anchors that extend within the central cavity 308 and a second pair of deployable anchors that deploy within the spinal defect 302A and engage the perimeter tissue 306 to maintain the position of the intradiscal shield 100C, 100D within spinal defect 302A.

Figure 4:
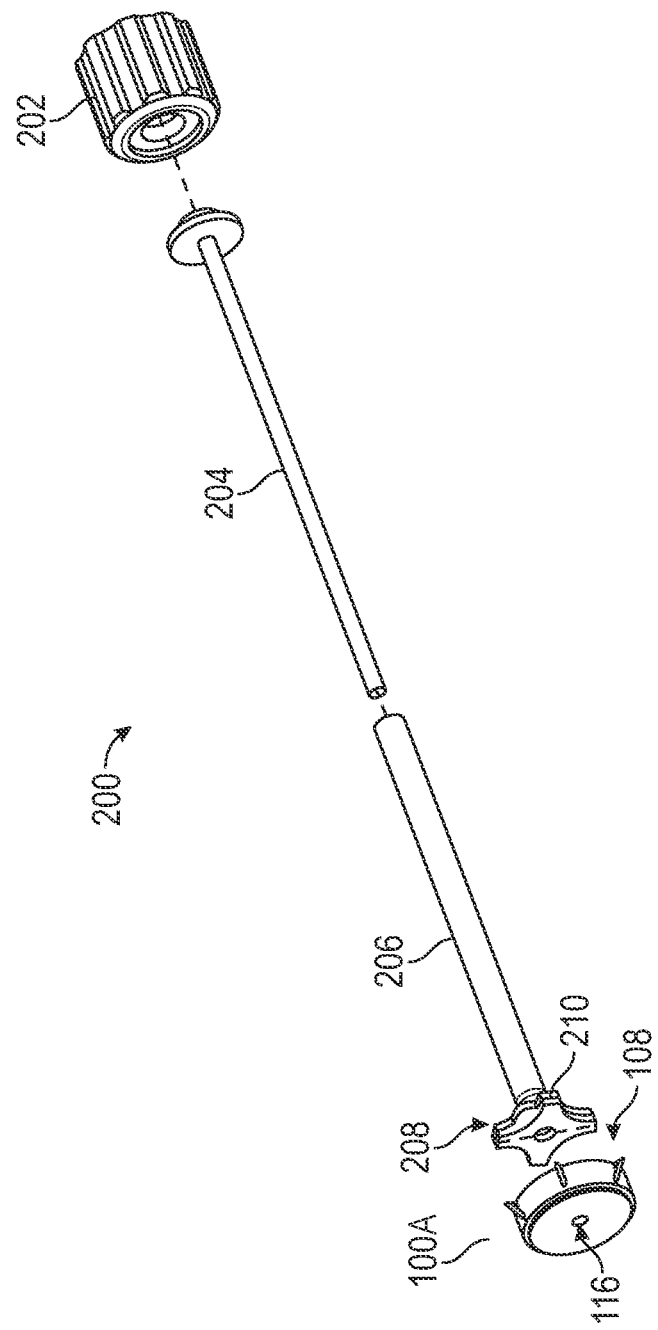
FIG. 4 depicts a blown out view of some embodiments of an insertion instrument.

FIG. 4 illustrates some embodiments of insertion instrument 200 in an exploded view. In some embodiments, insertion instrument 200 may include luer lock 202, shield bore opening device 204, shaft 206, and tip 208. In embodiments, luer lock 202 may be configured to attach to, or receive, a portion of a medical device, such as a syringe. The medical device/syringe may retain or include factors, liquids, materials, protein crosslinking reagent, or similar to be sprayed or otherwise placed into the central compartment of spinal disc 300. The shield bore opening device 204 may be located within the shaft 206 of insertion instrument 200. The shield bore opening device 204 may be configured to transition bore 116 from a closed configuration to an open configuration by rotation or axial displacement of the shield bore opening device 204. Alternatively, or additionally, the shield bore opening device 204 may be configured to transition bore 116 from an open configuration to a closed configuration. Alternatively, or additionally, the shield bore opening device 204 may be located on the outside of the shaft 206 of the insertion instrument 200.

Figure 5:
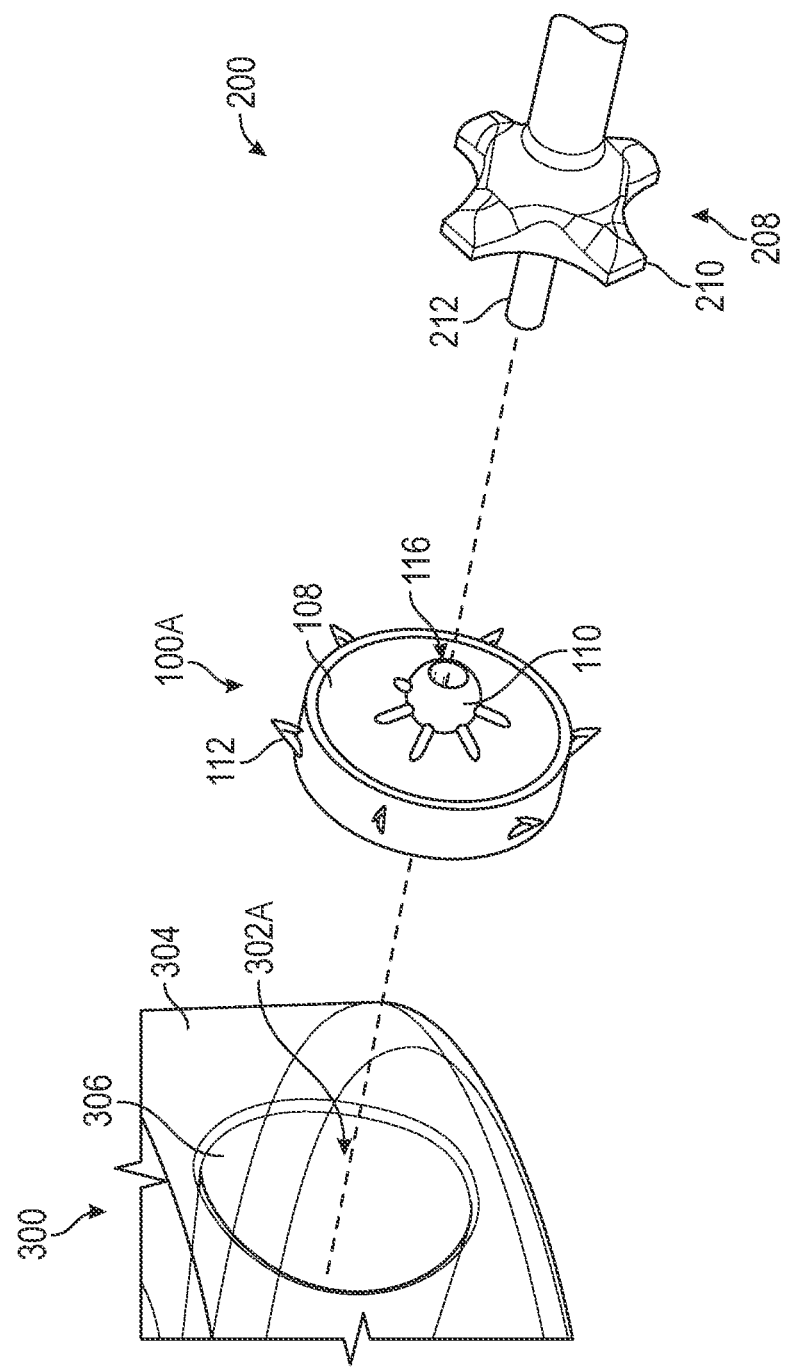
FIG. 5 illustrates some embodiments of a surgical system comprising the intradiscal shield and the insertion instrument prior to attachment.
Figure 6:
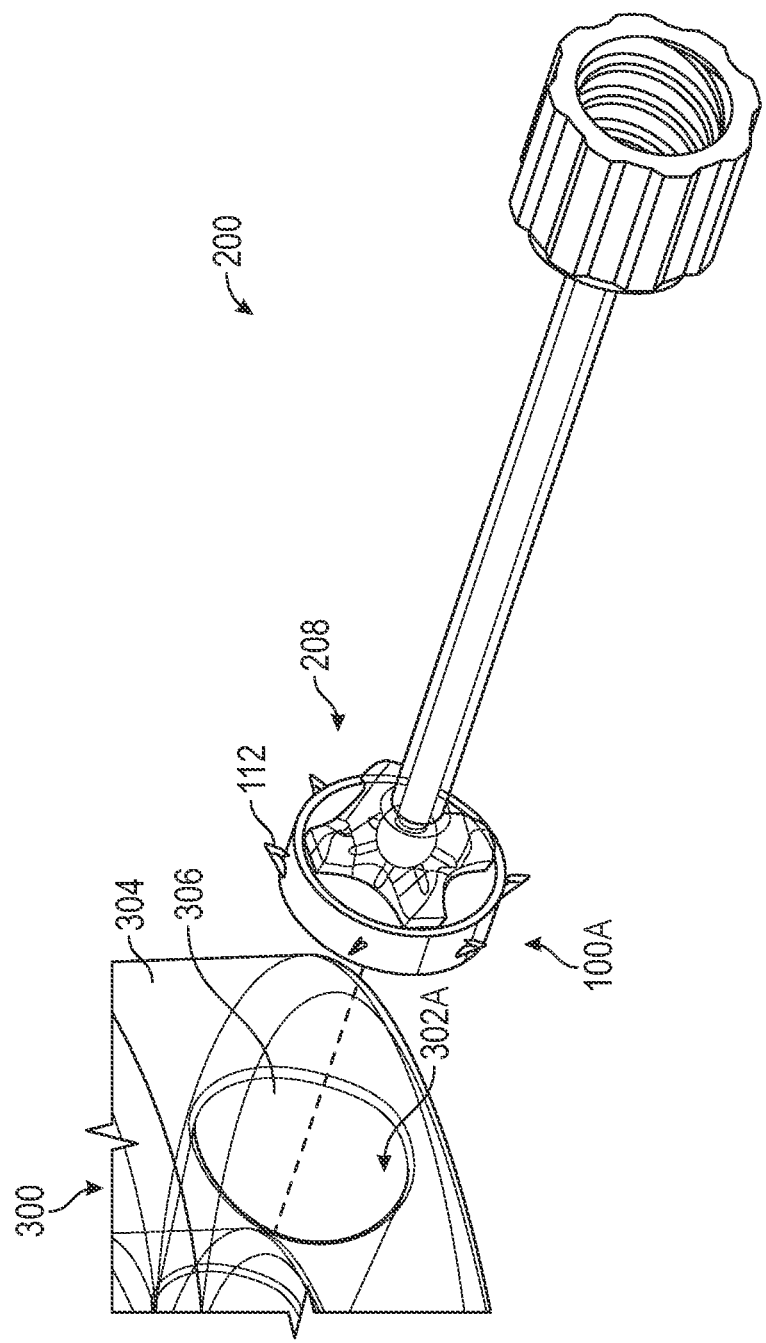
FIG. 6 illustrates some embodiments of the surgical system with the intradiscal shield attached to the insertion instrument.
Figure 8:
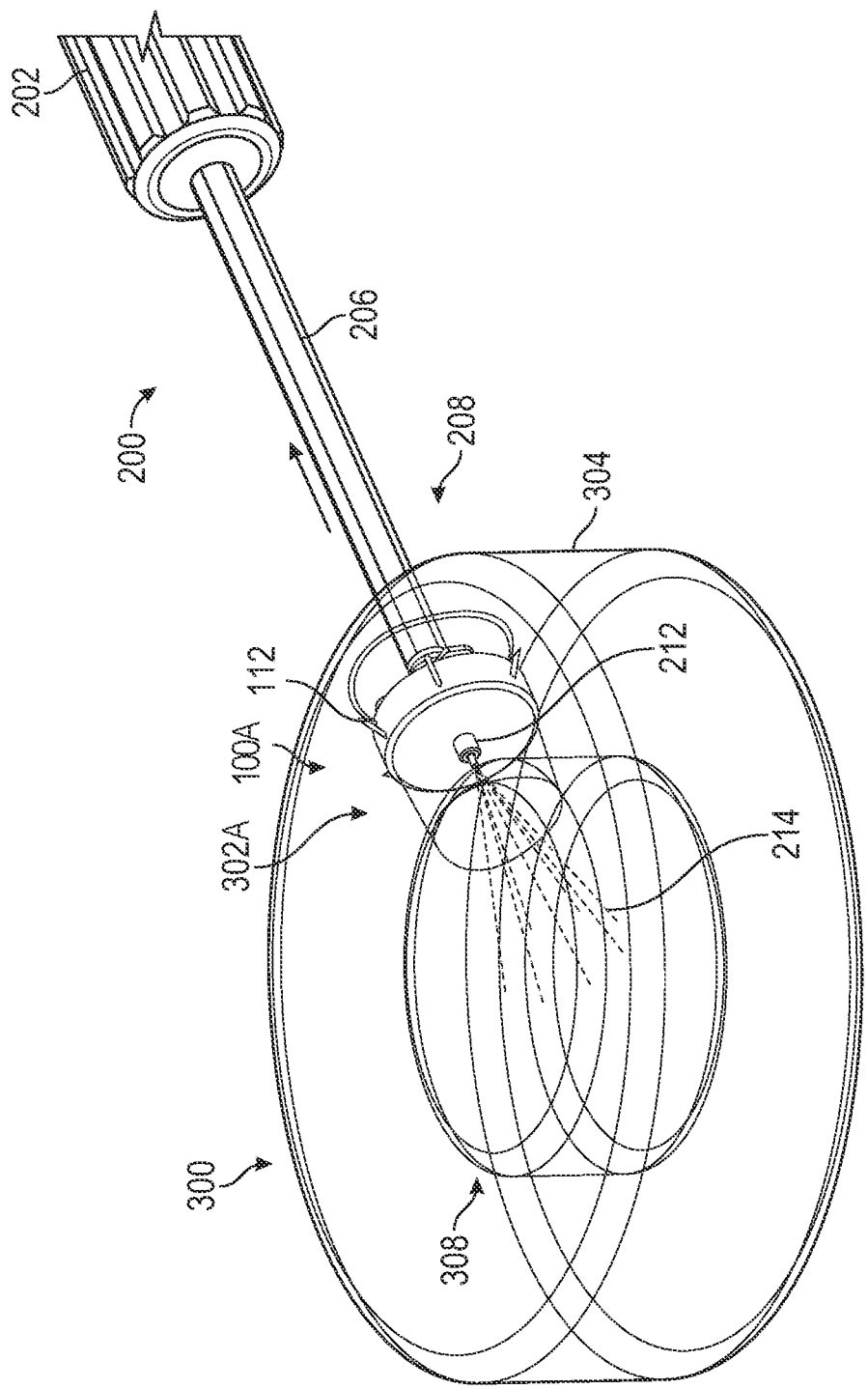
FIG. 8 illustrates some embodiments of insertion of the intradiscal shield into a spinal defect of a spinal disc.
Figure 9A:
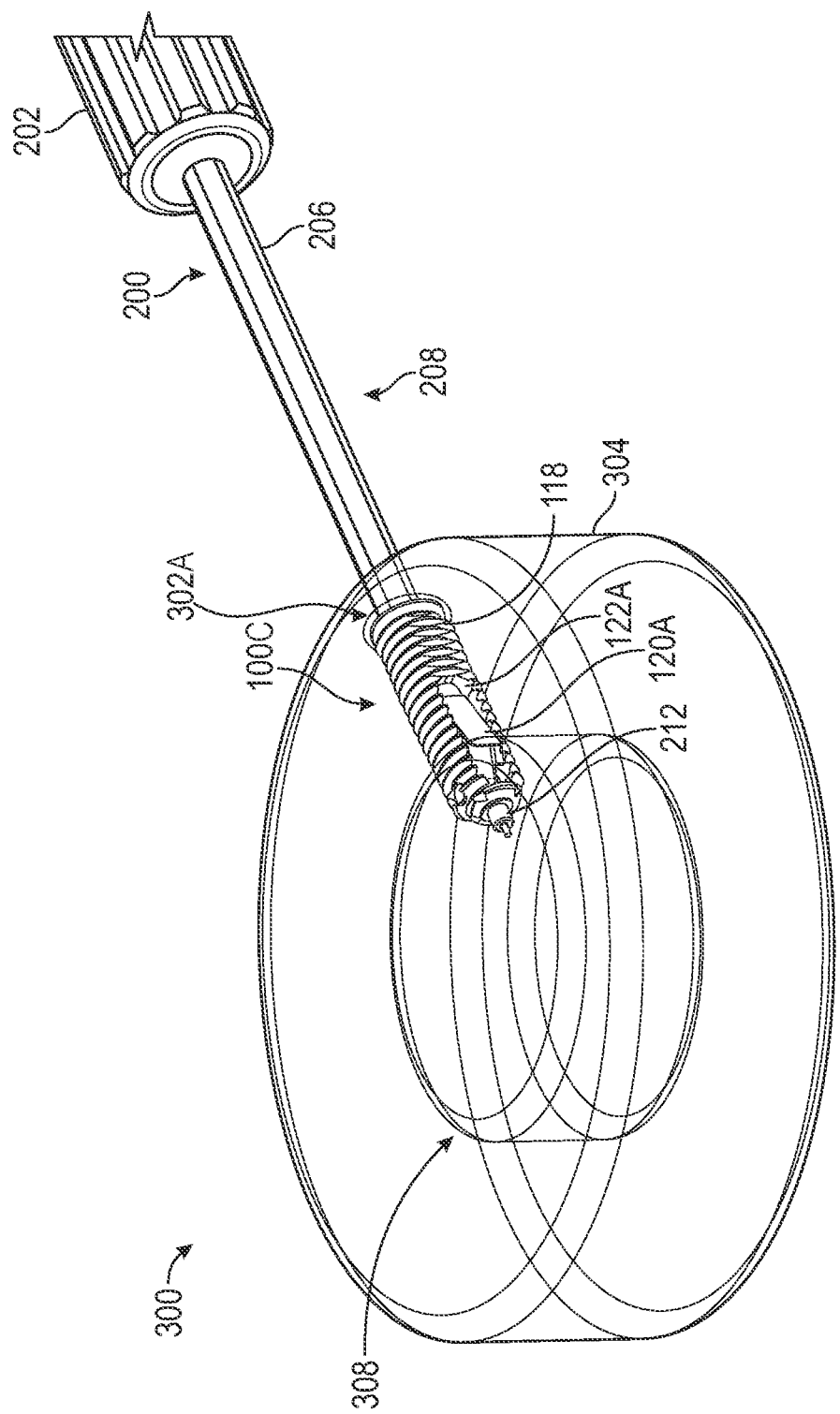
FIG. 9A illustrates some embodiments of insertion of an embodiment of the intradiscal shield comprising threads and deployable anchors into a spinal defect of a spinal disc.
Figure 9B:
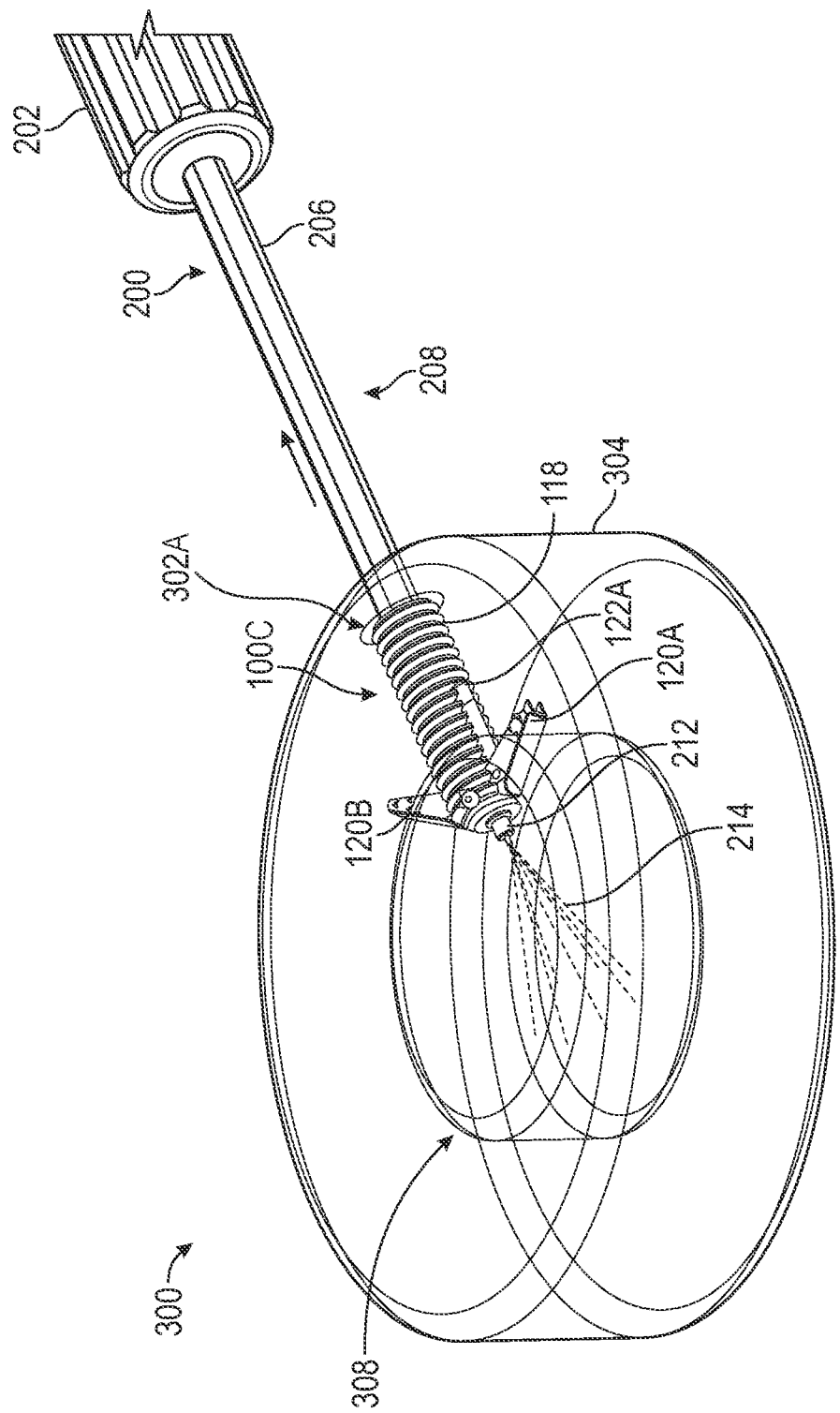
FIG. 9B illustrates some embodiments of deployment of the deployable anchors of an embodiment of the intradiscal shield in a spinal defect of a spinal disc.
Figure 10A:
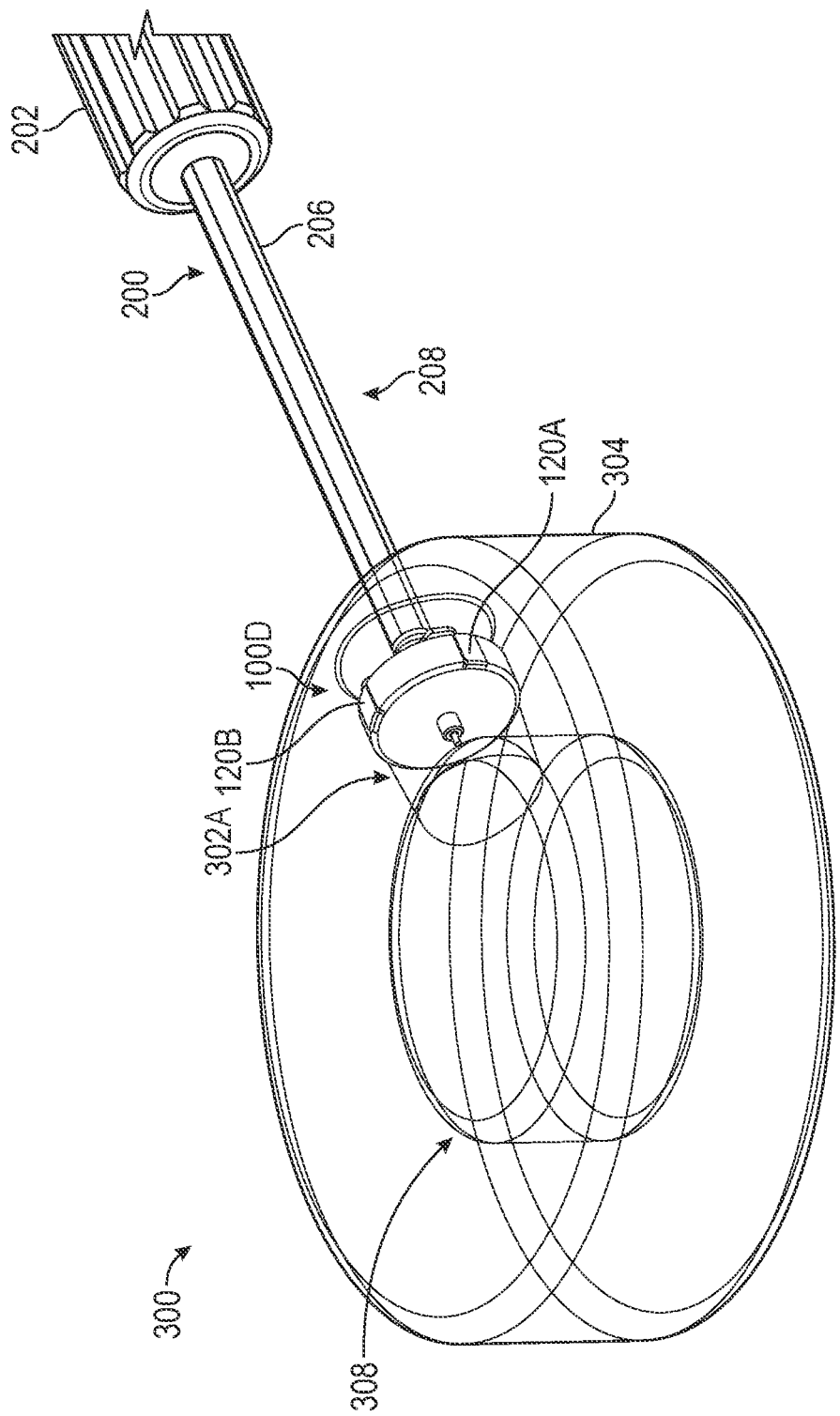
FIG. 10A illustrates some embodiments of insertion of an embodiment of the intradiscal shield comprising deployable anchors into a spinal defect of a spinal disc.
Figure 10B:
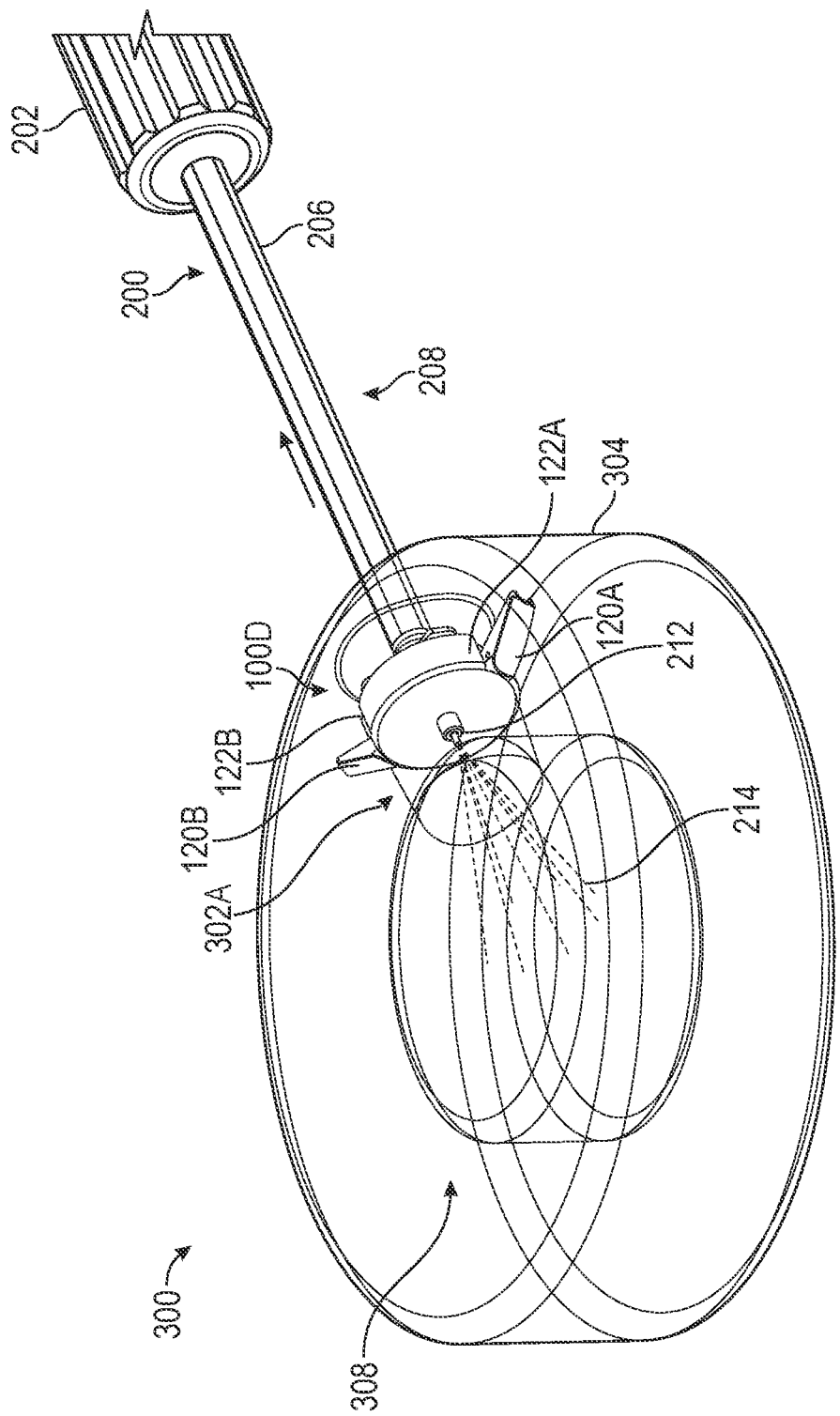
FIG. 10B illustrates some embodiments of deployment of the deployable anchors of an embodiment of the intradiscal shield in a spinal defect of a spinal disc.

FIG. 5 illustrates a surgical system configured to insert a shield into a spinal defect. The surgical system may comprise insertion instrument 200 and intradiscal shield 100A, 100B, 100C, 100D. FIG. 5 illustrates portions of insertion instrument 200 prior to engaging intradiscal shield 100A. FIGS. 6 and 7 illustrate insertion instrument 200 following engagement of intradiscal shield 100A. FIG. 8 illustrates some embodiments of insertion of intradiscal shield 100A into spinal defect 302A. FIG. 9A illustrates some embodiments of insertion of intradiscal shield 100C comprising threads 118 and deployable anchors 120A, 120B into spinal defect 302A. FIG. 9B illustrates some embodiments of intradiscal shield 100C with threads 118 and deployable anchors 120A, 120B in a deployed configuration in a spinal defect 302A. Examples of deployable anchors 120A, 120B are described in U.S. Pat. Nos. 9,757,164, 9,861,399, 11,311,388, 11,534,310, 9,314,276, and 9,907,581, which are incorporated by reference. FIG. 10A illustrates some embodiments of insertion of intradiscal shield 100D with deployable anchors 120A, 120B into spinal defect 302A. FIG. 10B illustrates some embodiments of intradiscal shield 100D with deployable anchors 120A, 120B in a deployed configuration in a spinal defect 302A. FIG. 11 illustrates some embodiments of intradiscal shield 100A seated within spinal defect 302A. As such, FIGS. 5-8, 9A-9B, 10A-10B, and 11 are best viewed together for the following description. As mentioned previously, tip 208 of insertion instrument 200 is configured to transiently engage intradiscal shield 100A, 100B, 100C, 100D for insertion into and placement of intradiscal shield 100 within spinal defect 302A.

In some embodiments, tip 208 includes one or more extensions 210 and may include spraying end 212. Extensions 210 may be configured to engage second side 108 so as to stabilize the connection between intradiscal shield 100A, 100B, 100C, 100D and insertion instrument 200. For example, during insertion of intradiscal shield 100A, 100B, 100C, 100D into spinal defect 302A (e.g., see FIG. 6), extensions 210 may transfer forces exerted on insertion instrument 200 to second side 108. Said another way, extensions 210 may increase the contact surface area between tip 208 and second side 108. As such, extensions 210 may aid in preventing caving in of intradiscal shield 100A, 100B, 100C, 100D while being placed within spinal defect 302A. Extensions 210 may also aid to keep the intradiscal shield 100A, 100B, 100D perpendicular to the long axis of the insertion instrument 200 while being placed within the spinal defect 302A.

Furthermore, as mentioned above, tip 208 is configured to transiently engage instrument engagement member 110 so as to allow attachment of intradiscal shield 100A, 100B, 100C, 100D to insertion instrument 200. Such attachment may be controlled via insertion instrument 200 so that intradiscal shield 100 stays attached to insertion instrument 200 until acted upon by a user of insertion instrument 200. For example, a mechanical button, switch, knob, or similar may allow for release of instrument engagement member 110 and thus intradiscal shield 100A, 100B, 100C, 100D from tip 208. In some embodiments, tip 208 may comprise a hook attachment configuration. Instrument engagement member 110 may comprise a matching loop configuration, thereby allowing attachment of tip 208 to instrument engagement member 110. In some embodiments, attachment of instrument engagement member 110 to tip 208 may be of a friction-fit nature, such that intradiscal shield 100A, 100B, 100C, 100D stays attached to insertion instrument 200 until such a force is exerted in the proximal direction (e.g., arrow in FIG. 8) so as to disconnect instrument engagement member 110 from tip 208. For example, upon inserting intradiscal shield 100A, 100B, 100C, 100D into spinal defect 302A, a user may pull insertion instrument 200 proximally (i.e., away from the center of spinal disc 300; see arrow in FIG. 8). As discussed above, in some embodiments, such proximal motion may cause anchors 112 to engage the perimeter tissue 306 of spinal defect 302A. This may seat intradiscal shield 100A, 100B within spinal defect 302A, so that further motion of insertion instrument 200 in the proximal direction may cause tip 208 to disengage instrument engagement member 110.

In some embodiments, bore 116 may be configured to receive spraying end 212 therethrough. As mentioned above, spraying end 212 may maintain bore 116 in an open configuration while received therethrough. As such, with bore 116 in the open configuration and spraying end 212 extending therethrough, spraying end 212 may release, or spray, factors into central cavity 308. For example, in some embodiments, a liquid 214 comprising a protein crosslinking reagent, such as a buffered liquid containing genipin, may be sprayed through insertion instrument 200 via shaft 206, which may be a hollow tube, and spraying end 212 and into central cavity 308 (see, e.g., FIG. 8). Such release of liquid 214 with a protein crosslinking reagent into central cavity 308, while intradiscal shield 100A, 100B, 100C, 100D is seated into spinal defect 302A, maintains the protein crosslinking reagent within central cavity 308 as intradiscal shield 100A, 100B, 100C, 100D is blocking diffusion of the protein crosslinking reagent out of spinal defect 302A. Furthermore, upon proximal movement of insertion instrument 200 (i.e., arrow in FIG. 8), spraying end 212 may be removed from bore 116, thereby bore 116 transitions to a closed configuration and prevents the released protein crosslinking reagent from diffusing out of central cavity 308 via spinal defect 302A (e.g., see FIG. 11). As mentioned above, release of the protein crosslinking reagent within central cavity 308 may aid in stabilization of spinal disc 300 and the spinal joint as a whole following surgery.

In some embodiments, after insertion of intradiscal shield 100C, 100D, deployable anchors 120A, 120B may deploy to a deployed configuration (see FIGS. 9B, 10B) to maintain the position of the intradiscal shield 100C, 100D within spinal defect 302A. Further, in some embodiments, deployable anchors 120A, 120B may deploy and engage with tissue in the spinal defect 302A to maintain the position of the intradiscal shield 100C, 100D within spinal defect 302A, as shown in FIG. 10B. Alternatively, or additionally, embodiments are contemplated in which intradiscal shield 100C extends through spinal defect 302A into central cavity 308, such that at least part of intradiscal shield 100C is within the central cavity 308 of spinal disc 300 (as shown in FIG. 9B). Further, in some embodiments, intradiscal shield 100C may completely fill the volume of spinal defect 302A. As such, deployable anchors 120A, 120B may deploy within central cavity 308 to maintain the position of the intradiscal shield 100C within spinal defect 302A. The deployable anchors 120A, 120B may comprise sharp protrusions extending therefrom that are configured to engage with tissue of the central cavity 308 or tissue of the spinal defect 302A.

In some embodiments, deployment of deployable anchors 120A, 120B may be controlled via insertion instrument 200 such that deployable anchors 120A, 120B stay in a stored configuration within substantially rectangular windows 122A, 122B until acted upon by a user of insertion instrument 200. For example, a mechanical button, switch, knob, or similar may allow for the transition of deployable anchors 120A, 120B into a deployed configuration. Alternatively, or additionally, in some embodiments, deployable anchors 120A, 120B are deployed utilizing a force exerted in the proximal direction (e.g., see arrow in FIG. 9B). For example, upon inserting intradiscal shield 100C, 100D into spinal defect 302A, a user may pull insertion instrument 200 proximally (i.e., away from the center of spinal disc 300; see arrow in FIG. 10B). In some embodiments, such proximal motion may cause deployable anchors 120A, 120B to transition from a stored configuration to a deployed configuration and engage the perimeter tissue 306 of spinal defect 302A or tissue within central cavity 308. This may seat intradiscal shield 100C, 100D within spinal defect 302A, such that further motion of insertion instrument 200 in the proximal direction may cause tip 208 to disengage instrument engagement member 110 of intradiscal shield 100C, 100D (not shown).

Figure 13:
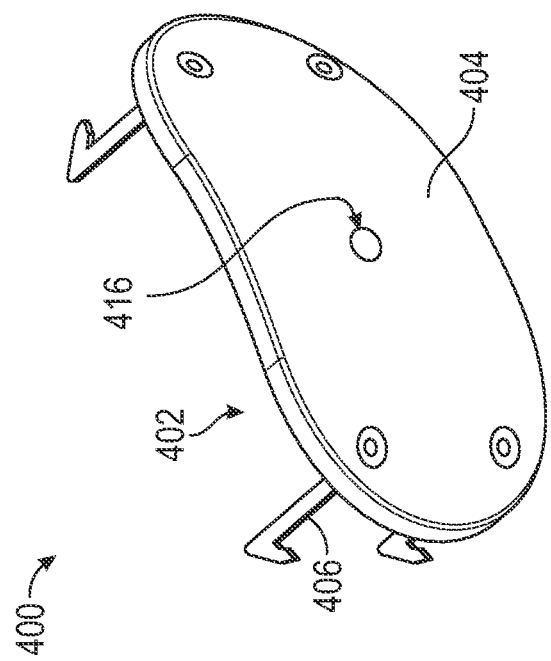
FIG. 13 depicts a perspective view from the exterior of the spinal disc of some embodiments of the exterior shield.
Figure 12:
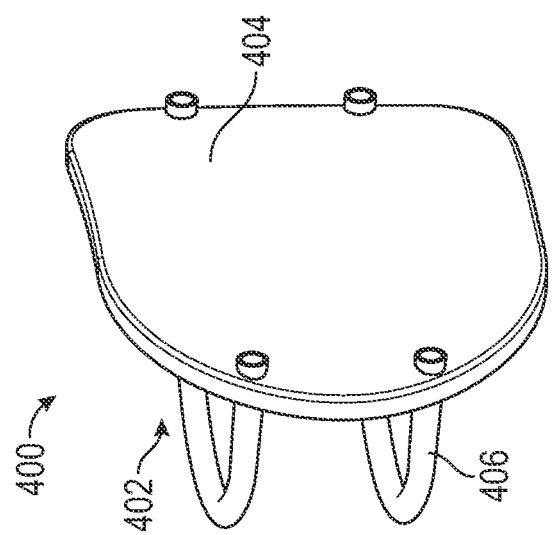
FIG. 12 depicts a perspective view from the exterior of the spinal disc of some embodiments of an exterior shield.
Figure 14A:
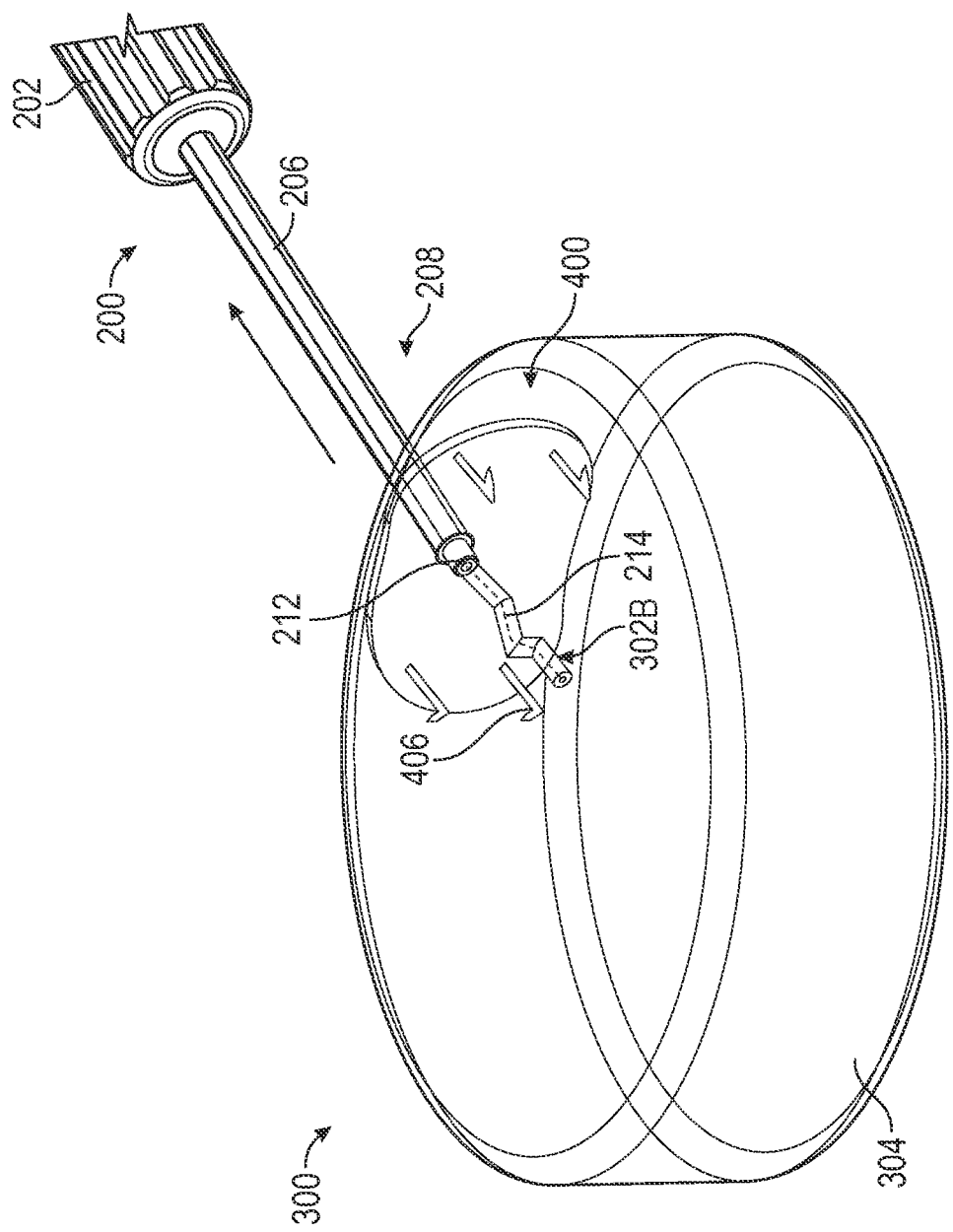
FIG. 14A illustrates some embodiments of attachment of the exterior shield to the spinal disc.
Figure 14C:
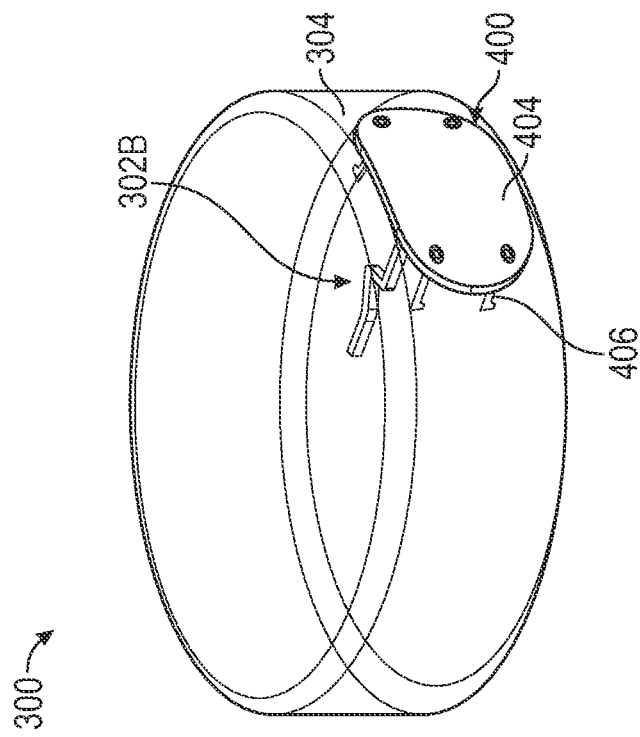
FIG. 14C illustrates some embodiments of the exterior shield attached to the spinal disc.
Figure 14B:
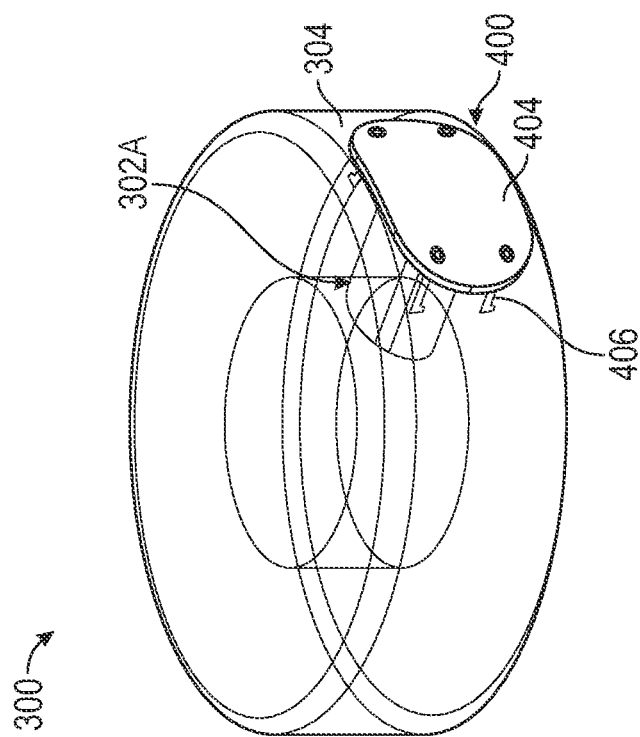
FIG. 14B illustrates some embodiments of the exterior shield attached to the spinal disc.
Figure 15A:
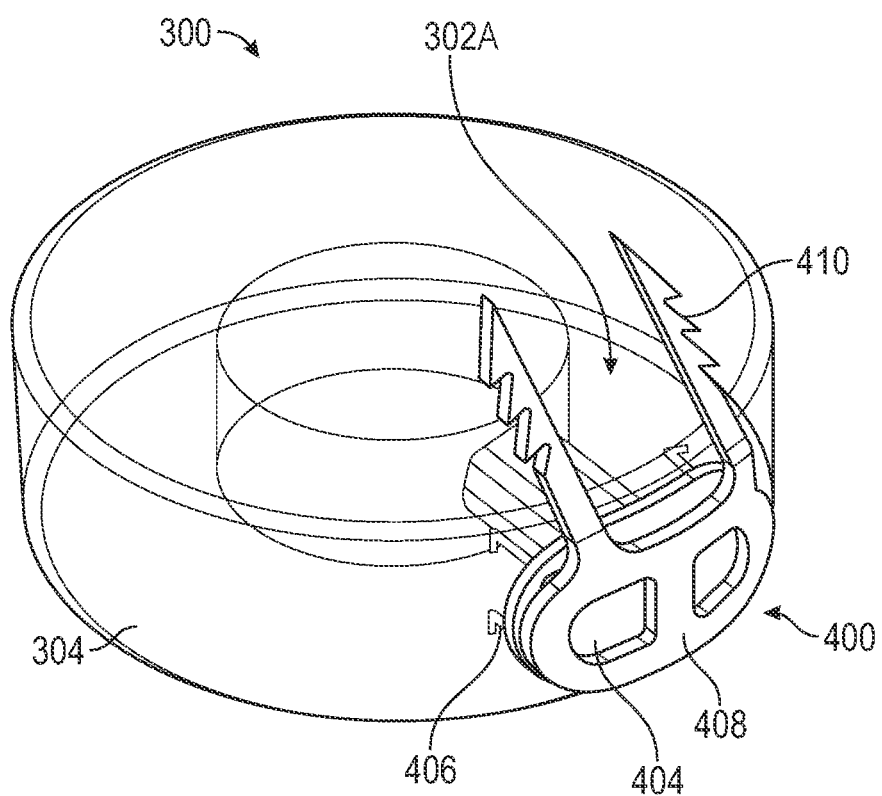
FIG. 15A illustrates some embodiments of the exterior shield attached to the spinal disc.
Figure 15B:
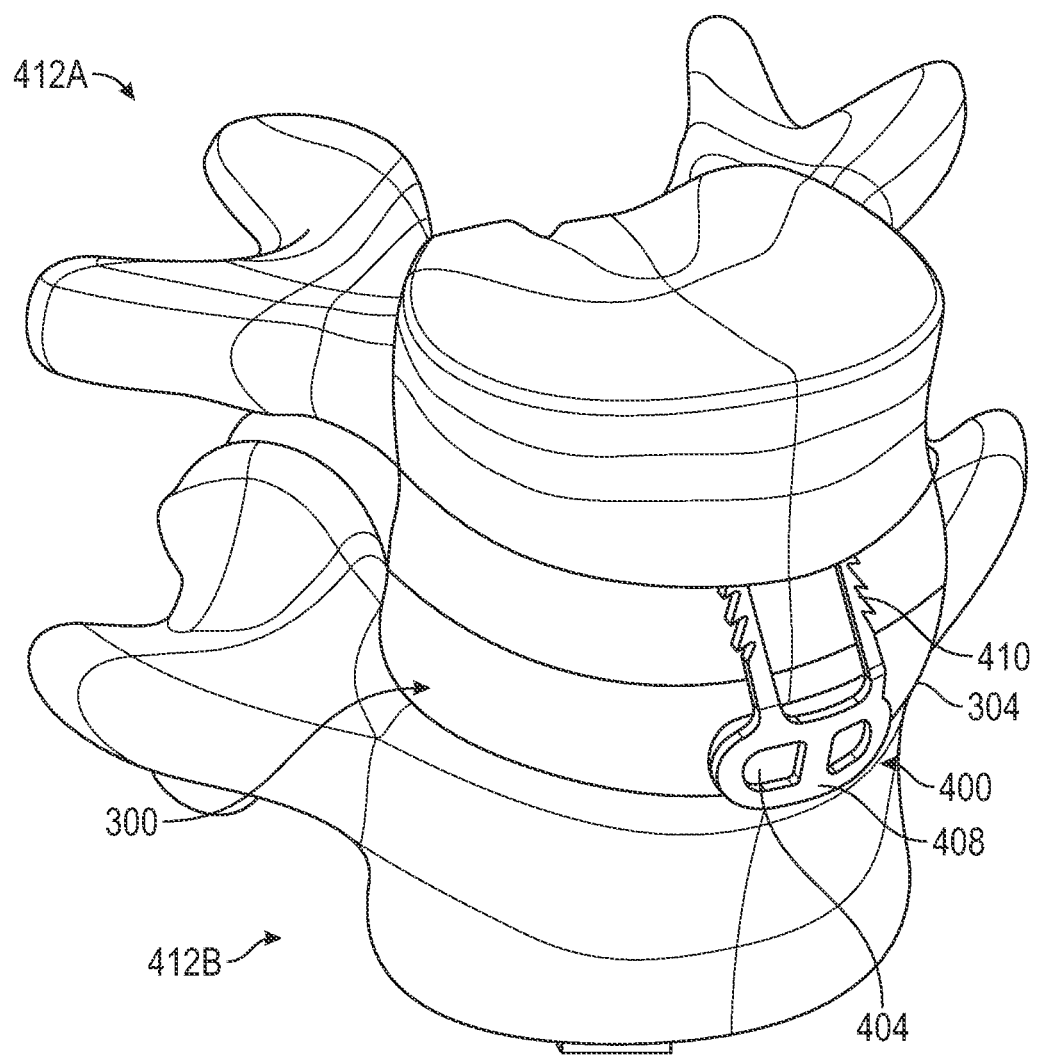
FIG. 15B illustrates some embodiments of the exterior shield attached to the spinal disc and an adjacent vertebra.

FIGS. 12 and 13 depict some embodiments of an exterior shield 400 for placement on the external portion of spinal defect 302A, 302B. FIG. 14A depicts exterior shield 400 being attached to spinal disc 300 and covering spinal defect 302B. FIGS. 14B-14C depict exterior shield 400 following attachment to spinal disc 300 and covering spinal defect 302A, 302B. FIG. 15A depicts some embodiments of exterior shield 400 attached to spinal disc 300. FIG. 15B depicts some embodiments of exterior shield 400 attached to spinal disc 300 and an adjacent vertebra 412A. Accordingly, FIGS. 12-15B are best viewed together for the following description.

In some embodiments, exterior shield 400 may be used to cover an external portion of spinal defect 302A, 302B. Exterior shield 400 may be used in conjunction with, or separately from, intradiscal shield 100A, 100B, 100C, 100D. As discussed above, spinal defect 302A may be formed during fenestration discectomy surgery and comprises a hole extending from the exterior wall 304 of spinal disc 300 into central cavity 308. As such, exterior wall 304 may be blocked, via exterior shield 400, to prevent or preclude re-herniation (see FIG. 14B). Similarly, disc herniation can be treated by a microdiscectomy surgery that removes the extruded disc materials but leaves only a small spinal defect 302B such as a clipped or cut surface of the disc near the penetrating tear or fissure through which the disc materials were extruded. As such, exterior wall 304 of damaged disc may be blocked, via exterior shield 400, to prevent re-herniation. For example, as depicted in FIG. 14C, exterior shield 400 blocks exterior wall 304 of damaged disc to prevent re-herniation by stabilizing the exterior wall 304 of the spinal disc 300. The spinal defect 302B, as depicted in FIG. 14C, may be a fissure left behind after a microdiscectomy surgery.

In some embodiments, exterior shield 400 includes first side 402, second side 404, and attachment mechanism 406. As mentioned above and as depicted in FIGS. 14A-15B, exterior shield 400 is configured to attach to exterior wall 304 and thereby block the opening of spinal defect 302A, 302B. Accordingly, exterior shield 400 is affixed to spinal disc 300 via attachment mechanism 406. In some embodiments, exterior shield 400 may be inserted and attached to exterior wall 304 using insertion instrument 200, or a similar insertion instrument having slight modifications. For example, as shown in FIG. 14A, exterior shield 400 may be inserted and attached to exterior wall 304 using insertion instrument 200. Alternatively, or additionally, in some embodiments, insertion instrument 200 is utilized to maintain a position of exterior shield 400 at the exterior wall 304 of the spinal disc 300 while an operator attaches exterior shield 400 to the exterior wall 304 of the spinal disc 300. In these embodiments, exterior shield 400 may be attached to exterior wall 304 via an adhesive (e.g., fibrin glue, cyanoacrylate, etc.), amine groups that interact with protein crosslinking reagents disposed on exterior wall 304, and/or sewing of exterior shield 400 to exterior wall 304, and/or tacking of exterior shield 400 to exterior wall 304, and/or tacking to exterior of vertebral bone above or below spinal disc. Exemplary attachments of exterior shield 400 to exterior wall 304 are further discussed below. In embodiments in which exterior shield 400 is sewn to exterior wall 304, a suture delivery device (not shown) may be used, as further discussed below.

While not depicted, exterior shield 400 may include similar components and features depicted with relation to intradiscal shield 100A, 100B, 100C, 100D. For example, exterior shield 400 may include an instrument engagement member similar to instrument engagement member 110, thereby facilitating attachment of exterior shield 400 to insertion instrument 200. In another example, exterior shield 400 may include a bore similar to bore 116, thereby allowing spraying end 212 to be inserted therethrough. For example, as shown in FIGS. 13 and 14A, exterior shield 400 may include a bore 416 such that spraying end 212 may be inserted therethrough. Bore 416, similar to bore 116 of intradiscal shield 100A, 100B, 100C, 100D, may be configured to transition between an open configuration and a closed configuration.

After exterior shield 400 has been secured to the spinal disc 300, spraying end 212 of insertion instrument 200 may be used to release, or spray, a liquid 214 containing a protein crosslinking reagent via bore 416 within the spinal defect 302A, 302B (as shown in FIG. 14A). Similarly to bore 116, bore 416 may be configured to receive spraying end 212 such that spraying end 212 may maintain bore 416 in an open configuration while received therethrough. In some embodiments, the liquid 214 comprising the protein crosslinking reagent may be a degradable polymer, biocompatible liquid, carrier material, as well as constituents thereof and combinations herein. For example, the protein crosslinking reagent may comprise genipin and may be dissolved in a buffered carrier, such as EPPS-Phosphate, as further discussed below. Such release of liquid 214 with a protein crosslinking reagent into spinal defect 302A, 302B, while exterior shield 400 is secured to spinal disc 300, maintains the protein crosslinking reagent within spinal defect 302A, 302B as exterior shield 400 is blocking diffusion of the protein crosslinking reagent out of spinal defect 302A, 302B. Furthermore, upon proximal movement of insertion instrument 200 (i.e., arrow in FIG. 14A), spraying end 212 may be removed from bore 416, thereby bore 416 transitions to a closed configuration and prevents the released protein crosslinking reagent from diffusing out of spinal defect 302A, 302B. As mentioned above, release of the protein crosslinking reagent within spinal defect 302A, 302B may aid in stabilization of spinal disc 300 and the spinal joint as a whole following surgery.

In embodiments depicted herein, attachment mechanism 406 of exterior shield 400 comprises a suture that enters spinal disc 300 through lateral side of exterior shield 400 then arcs across the interior annulus tissue (e.g., through exterior wall 304 and spinal defect 302A, 302B) and exits spinal disc 300 and subsequently exits through the medial side of exterior shield 400. In some embodiments, attachment mechanism 406 may be one or more barbed tacks that penetrate through the medial or lateral side of exterior shield 400 and enters into the spinal disc (e.g., through exterior wall 304). In some embodiments, exterior shield 400 contains barbed tacks attached to the sides of the exterior shield 400 projecting from the first side 402 of exterior shield 400. However, attachment mechanism 406 may comprise any material and/or method that maintains the position of exterior shield 400 along exterior wall 304 and blocks spinal defect 302A, 302B. Furthermore, attachment mechanism 406 may be coated in a degradable polymer containing a protein crosslinking reagent therein. For example, attachment mechanism 406 may comprise one or more barbed tacks coated with a degradable polymer containing a protein crosslinker. In another example, exterior shield 400 may be sewn and/or adhered to exterior wall 304. In some embodiments, exterior shield 400 may be sewn to exterior wall 304 using sutures coated with a degradable polymer containing a protein crosslinking reagent therein, such as those disclosed in U.S. Pat. No. 10,278,947, which is hereby incorporated by reference in its entirety. In embodiments in which exterior shield 400 is sewn to exterior wall 304, a suture delivery device (not shown) may be used. For example, a curved needle attached to one end of the coated suture may be used. For descriptive purposes, the suture delivery device may enter spinal disc 300 through the lateral or medial side of exterior shield 400. The suture delivery device may then arc across the interior annulus tissue and exit through the medial or lateral side of exterior shield 400. In some embodiments, a knot or ball, or other terminal device at the distal end of the suture would prevent the distal end from being pulled through the side of exterior shield 400 by the suture delivery device. In some embodiments, the needle used to insert sutures may be curved and shaped appropriately to enter through one side of exterior shield 400, arc across the interior of spinal disc 300, and exit through an opposing side of exterior shield 400. In some embodiments, the curved needle may have an axially aligned notch or colored stripe or detachable guide at the proximal base of the curved needle to enable the operator of the insertion device to prevent rotation of the curved needle and enable the distal end of the curved needle to remain on approximately the same plane as the proximal end of the curved needle. Alternatively, the tip 208 of insertion instrument 200 that transiently attaches to the exterior shield 400 may have a means of holding the curved needle and preventing rotation of the needle as it is delivered through the side of the exterior shield 400, through the spinal disc 300, and through the other side of the exterior shield 400.

In some embodiments, exterior shield 400 may be adhered to exterior wall 304 using a biocompatible adhesive material, such as fibrin glue, cyanoacrylate adhesive, or any other biocompatible adhesive material. Alternatively, and as discussed above, first side 402 may be coated with amine groups, while a protein crosslinking reagent is disposed on exterior wall 304. As such, the protein crosslinking reagent may interact with the amine groups, thereby bonding the amine functionalized polymer surface regions to exterior wall 304 and maintaining the position of exterior shield 400 thereon.

In some embodiments, and as depicted in FIGS. 12-15B, first side 402 is configured to face inwardly towards spinal defect 302A, 302B and central cavity 308. As such, in some embodiments, first side 402 may comprise, or be coated with, a degradable polymer. Additionally, the degradable polymer may be combined with a protein crosslinking reagent. In some embodiments, the protein crosslinking reagent may be embedded within the degradable polymer. In this manner, the protein crosslinking reagent may be released within spinal defect 302A, 302B and directly into the disc tissue around spinal defect 302A, 302B contacted by exterior shield 400 as the polymer degrades and similarly the protein crosslinking reagent may diffuse towards the center of spinal disc 300 or central cavity 308. As mentioned above, such release of a protein crosslinking reagent within spinal defect 302A, 302B and directly into disc tissue around spinal defect 302A, 302B may increase spinal joint stability and help with recovery of spinal disc 300 following surgery.

In some embodiments, exterior shield 400 may include vertebral engagement member 408. In some embodiments, vertebral engagement member 408 may be configured to mechanically stabilize exterior shield 400 with respect to one of adjacent vertebrae 412A, 412B. For example, vertebral engagement member 408 may include one or more sharp protrusions 410 extending therefrom, directed toward the center of one of adjacent vertebrae 412A, 412B. As such, one or more sharp protrusions 410 may engage the vertebral body of one of adjacent vertebrae 412A, 412B juxtaposed to spinal disc 300 and forming the spinal joint in which spinal disc 300 is located. In some embodiments, one or more sharp protrusions 410 include barbs, pins, or otherwise sharp extensions that may partially or fully embed within the vertebral body of one of adjacent vertebrae 412A, 412B.

As discussed above with reference to intradiscal shield 100A, 100B, 100C, 100D and exterior shield 400, a protein crosslinking reagent may be contained in a coating, or otherwise embedded within, any portion or component of intradiscal shield 100A, 100B, 100C, 100D and/or exterior shield 400 as well as be released/sprayed within spinal defect 302A, 302B and towards the center of spinal disc 300 via insertion instrument 200. For example, the protein crosslinking reagent may be released/sprayed within central cavity 308 via insertion instrument 200 (see, e.g., FIGS. 8, 9B, 10B). This protein crosslinking reagent may, in embodiments, include genipin. While genipin is used herein as an example of a protein crosslinking reagent, embodiments of the present disclosure may include any known biocompatible crosslinking reagent. In some embodiments, the protein crosslinking reagent (e.g., genipin) may be dissolved in a buffered carrier, such as EPPS-Phosphate. While EPPS-Phosphate is used as an example of a buffered carrier for the protein crosslinking reagent, embodiments of the present disclosure may include any known biocompatible buffered carrier capable of carrying the protein crosslinking reagent therein. Examples of particularly useful crosslinking reagents and their corresponding suspension media are disclosed in commonly assigned U.S. Pat. Nos. 10,278,947, 8,283,322, 8,198,248, 9,101,602, 9,084,772, 8,211,938, 8,153,600, 8,119,599, 9,918,870, 9,492,592, 8,450,276, 8,022,101, 7,435,722, and 10,980,771, the disclosures of which are all incorporated herein by reference in their entirety.

In some embodiments, exterior shield 400 may be made of any medical-grade materials such as medical-grade plastics, polycarbonates (PC), polypropylene (PP), polyethylene (PE), polyvinyl chloride (PVC), acrylonitrile butadiene styrene (ABS), polystyrene (PS), polyethylene terephthalate glycol (PETG), polymethyl methacrylate (PMMA), polyether ether ketone (PEEK), polymers, bioabsorbable material, metals, stainless steel, copper, titanium, cobalt chrome, aluminum, magnesium, additive manufactured materials, titanium-based alloys, cobalt-based alloys, nylon, thermoplastic polyurethane (TPU), polyphenylsulfone (PPSU), polyamide-imide (PAI), or any combinations thereof, as well as any other suitable medical-grade materials or constituents thereof. For example, in some embodiments, a portion or all of first side 402 may be made of a polymer, and potentially a degradable polymer, having a protein crosslinker, such as genipin, embedded therein. Embodiments are also contemplated in which a portion or all of the intradiscal shield 400 may be manufactured through additive manufacturing.

Figure 16:
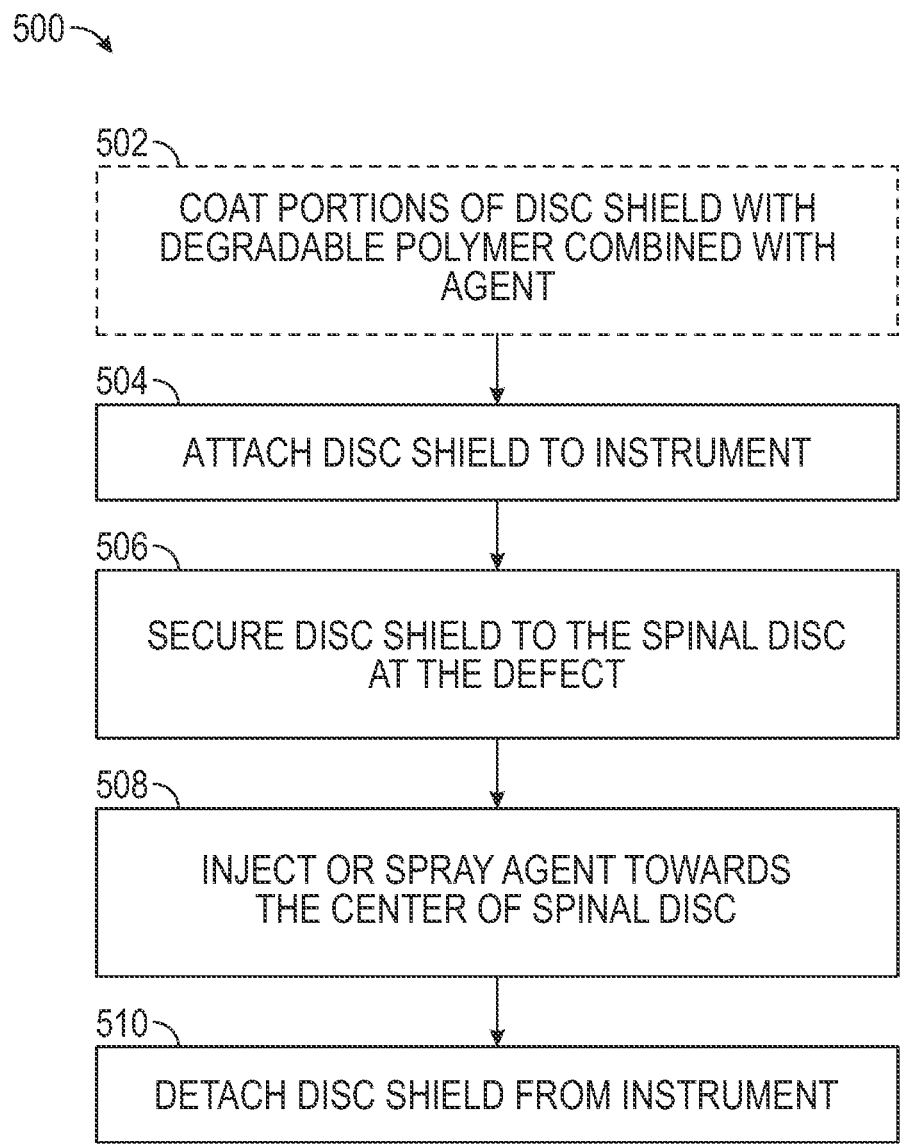
FIG. 16 is a flowchart relating to embodiments of the present disclosure illustrated, at least in part, in FIGS. 1-15B.

Now turning to FIG. 16, a method for providing structural integrity to a spinal disc having a spinal defect is depicted and referred to generally by reference numeral 500. As discussed herein, the term "disc shield" is used to refer to multiple embodiments disclosed herein. For example, intradiscal shield 100A, 100B, 100C, 100D and/or exterior shield 400 may be referred to as a "disc shield" or "disc shields" in this disclosure. At optional step 502, a portion or portions of a disc shield are coated with a degradable polymer combined with a protein crosslinking reagent. In an example of optional step 502, intradiscal shield 100A, 100B, 100C, 100D and/or exterior shield 400 are coated with a degradable polymer combined with a protein crosslinking reagent such as genipin. This may include portions of intradiscal shield 100A, 100B, 100C, 100D and exterior shield 400 that face inwardly towards spinal defect 302A, 302B as well as portions that contact spinal disc 300. Alternatively, or additionally, the protein crosslinking reagent may be embedded in portions of intradiscal shield 100A, 100B, 100C, 100D and/or exterior shield 400 that include a degradable polymer.

At step 504, the disc shield is attached to an insertion instrument. In an example of step 504, intradiscal shield 100A, 100B, 100C, 100D and/or exterior shield 400 is attached to insertion instrument 200. In some embodiments, attachment of intradiscal shield 100A, 100B, 100C, 100D and/or exterior shield 400 occurs at tip 208. In some embodiments, spraying end 212 may be inserted through bore 116 located within intradiscal shield 100A, 100B, 100C, 100D and defined by inner portion 104 and/or instrument engagement member 110. Furthermore, in some embodiments, tip 208 of insertion instrument 200 may transiently attach to instrument engagement member 110 of intradiscal shield 100A, 100B, 100C, 100D. Embodiments are also contemplated in which the spraying end 212 may be inserted through bore 416 of exterior shield 400.

At step 506, the disc shield is secured to the spinal disc at the site of the spinal defect 302A, 302B. In an example of step 506, intradiscal shield 100A, 100B, 100C, 100D is inserted within spinal defect 302A. In some embodiments, insertion may be performed surgically by using insertion instrument 200. For example, tip 208 and shaft 206 may be inserted through an endoscopic aperture and cannula placed within the patient's body and leading from the exterior to the site of spinal defect 302A. In this example, intradiscal shield 100A, 100B, 100C, 100D is subsequently secured within spinal defect 302A by processes described above. For example, one or more anchors 112 disposed on intradiscal shield 100A, 100B, 100C, 100D are seated into the perimeter tissue 306 of the spinal defect. In an example of step 506, an operator of insertion instrument 200 may translate insertion instrument 200 proximally (i.e., direction of arrow depicted in FIG. 8). As such, proximal translation of insertion instrument 200 also translates intradiscal shield 100A, 100C, 100D partially. Proximal movement of intradiscal shield 100A, 100C, 100D within spinal defect 302A may cause anchors 112 to seat within the perimeter tissue 306 of spinal defect 302A. Additionally, or alternatively, and as described above, intradiscal shield 100A, 100B, 100D may be sewn and/or adhered within spinal defect 302A. Such seating of intradiscal shield 100A, 100B, 100C, 100D within spinal defect 302A is meant to maintain the position of intradiscal shield 100A, 100B, 100C, 100D while also preventing any material within central cavity 308 and spinal defect 302A from diffusing outwardly through spinal defect 302A.

In another example of step 506, exterior shield 400 is secured to spinal disc 300 at the site of spinal defect 302A, 302B. For example, and as described above, an operator of a surgical instrument (e.g., insertion instrument 200) may sew exterior shield 400 to the exterior wall 304 of spinal disc 300 such that exterior shield 400 completely covers spinal defect 302A, 302B. In this case, the sutures used to sew exterior shield 400 to spinal disc 300 may be coated with a degradable polymer containing a protein crosslinking reagent. Additionally, or alternatively, exterior shield 400 having barbed pins as attachment mechanism 406 may be distally pressed into spinal disc 300 such that the barbed pins (i.e., attachment mechanism 406) are fully inserted into tissue of spinal disc 300 and secured therein. Furthermore, in some examples of step 506, exterior shield 400 may include vertebral engagement member 408. In these examples, one or more sharp protrusions 410 of vertebral engagement member 408 may be pressed against, or otherwise secured to an adjacent vertebral body of one of adjacent vertebrae 412A, 412B surrounding spinal disc 300. Such securing of exterior shield 400 to spinal disc 300 is meant to maintain the position of exterior shield 400 while also preventing any material within central cavity 308 and/or spinal defect 302A, 302B from diffusing outwardly through spinal defect 302A, 302B.

At step 508, a protein crosslinking reagent is sprayed, or otherwise released or injected, towards the center of the spinal disc. For example, the protein crosslinking reagent may be sprayed towards the center of the spinal disc through spinal defect 302A, 302B. In another example, the protein crosslinking reagent may be sprayed within the central cavity 308 of spinal disc 300. In an example of step 508, a protein crosslinking reagent (e.g., genipin dissolved in EPPS-Phosphate) is sprayed through shaft 206 and out of spraying end 212. As spraying end 212 is inserted through bore 116, the protein crosslinking reagent is sprayed distally to intradiscal shield 100A, 100B, 100C, 100D and towards the center of the spinal disc 300. For example, the protein crosslinking reagent is sprayed into central cavity 308. As intradiscal shield 100A, 100B, 100C, 100D is blocking material from exiting spinal disc 300 via spinal defect 302A, the protein crosslinking reagent is maintained therein.

In another example of step 508, exterior shield 400 includes a bore 416 similar to bore 116 such that spraying end 212 is inserted into and received therethrough. Similarly, such a configuration allows for the protein crosslinking reagent to be sprayed or injected distally to exterior shield 400 and towards the center of the spinal disc. As exterior shield 400 is blocking material from exiting spinal disc 300 via spinal defect 302A, 302B, the protein crosslinking reagent is maintained therein. In some embodiments, step 508 may be performed prior to step 506.

At step 510, the disc shield is detached from the insertion instrument. In an example of step 510, intradiscal shield 100A, 100B, 100C, 100D is attached to insertion instrument 200 via a friction-fit between instrument engagement member 110 and tip 208. As such, in this example, a user may apply enough force to overcome the friction fit between instrument engagement member 110 and tip 208, thereby detaching intradiscal shield 100A, 100B, 100C, 100D from insertion instrument 200 and leaving intradiscal shield 100A, 100B, 100C, 100D seated within spinal defect 302A. In another example of step 510, a user may actuate one or more release mechanisms (e.g., lever, button, etc.) disposed on insertion instrument 200 which subsequently actuates an attachment component disposed at tip 208. Upon actuation via the release mechanism, the attachment component (not shown) may release instrument engagement member 110, thereby detaching intradiscal shield 100A, 100B, 100C, 100D from insertion instrument 200.

In another example of step 510, exterior shield 400 is attached or maintained to tip 208 of insertion instrument 200. Similar to the above example, an operator of insertion instrument 200 may actuate one or more release mechanisms of insertion instrument 200 such that exterior shield 400 is detached from tip 208. In some embodiments, detachment of the disc shield from insertion instrument 200 may transition the disc shield from an open configuration to a closed configuration. For example, spraying end 212 may be inserted into bore 116 of intradiscal shield 100A, 100B, 100C, 100D. As such, distal translation of spraying end 212 out of bore 116 may cause bore 116 to close and thus be in a closed configuration. Similarly, spraying end 212 may be inserted into a bore 416 located in exterior shield 400. As such, removal of spraying end 212 from bore 416 disposed on exterior shield 400 may cause bore 416 to transition from an open configuration to a closed configuration.

As mentioned above and for purposes of clarity, in some embodiments, both intradiscal shield 100A, 100B, 100C, 100D and exterior shield 400 may be used to provide structural integrity to spinal defect 302A, 302B. As such, in some examples of the steps listed above, both intradiscal shield 100A, 100B, 100C, 100D and exterior shield 400 may be sequentially or concurrently attached to spinal disc 300.

Features described above as well as those claimed below may be combined in various ways without departing from the scope hereof. The following examples illustrate some possible, non-limiting combinations:

(A1) An intradiscal shield configured to provide structural integrity to a spinal disc having a spinal defect, the intradiscal shield comprising: an outer barrier defining an inner portion, wherein the inner portion defines a bore; a first side configured to face a central cavity of the spinal disc; a second side, opposite the first side, and configured to face outwardly from the central cavity, wherein the second side comprises an instrument engagement member, wherein the bore extends through the inner portion and the instrument engagement member; and one or more anchors extending from the outer barrier and configured to maintain a position of the intradiscal shield within the spinal defect, wherein the bore is configured to transition between an open configuration and a closed configuration, wherein, in the open configuration, the bore provides an opening for spraying a protein crosslinking reagent therethrough.

(A2) For the intradiscal shield denoted as (A1), wherein the bore biases into the closed configuration, wherein the spinal defect is a surgical defect.

(A3) For the intradiscal shield denoted as (A1) or (A2), wherein the bore is configured to transition into the open configuration upon interaction with an insertion instrument, wherein, in the open configuration, the bore receives the protein crosslinking reagent to thereby release the protein crosslinking reagent into the central cavity of the spinal defect, such that the protein crosslinking reagent stabilizes the spinal disc.

(A4) For the intradiscal shield denoted as any of (A1) through (A3), wherein the one or more anchors are angled acutely towards the second side, wherein the one or more anchors are configured to insert into a perimeter tissue of the spinal defect to maintain the position of the intradiscal shield within the spinal defect.

(A5) For the intradiscal shield denoted as any of (A1) through (A4), wherein the instrument engagement member comprises one or more stabilizers, wherein the one or more stabilizers are configured to stabilize the intradiscal shield.

(A6) For the intradiscal shield denoted as any of (A1) through (A5), wherein one or more of the outer barrier or the first side comprise a coating of a degradable polymer having a protein crosslinker contained therein.

(B1) A surgical system configured to insert an intradiscal shield into a spinal defect of a spinal disc, the surgical system comprising: the intradiscal shield, comprising: an outer barrier; an inner portion defined within the outer barrier, the inner portion having a first side configured to face inwardly within the spinal defect and a second side configured to face outwardly from the spinal defect; an instrument engagement member disposed on the second side; and a bore defined by the inner portion and the instrument engagement member, the bore configured to transition between an open configuration and a closed configuration; and an insertion instrument, comprising: a luer lock disposed at a proximal end; a shaft extending distally from the luer lock and defining a hollow tube therein; a distal tip configured to transiently attach to the instrument engagement member of the intradiscal shield; and a spraying end comprised in the distal tip, wherein the bore of the intradiscal shield is configured to receive the spraying end of the insertion instrument to thereby maintain the bore in the open configuration, wherein the spraying end sprays a protein crosslinker through the bore when the bore is in the open configuration.

(B2) For the surgical system denoted as (B1), wherein the spraying end sprays the protein crosslinker through the bore into the spinal defect when the bore is in the open configuration, to thereby stabilize the spinal disc having the spinal defect.

(B3) For the surgical system denoted as (B1) or (B2), the intradiscal shield further comprising: one or more anchors disposed on the outer barrier and configured to maintain a position of the intradiscal shield within the spinal defect.

(B4) For the surgical system denoted as any of (B1) through (B3), wherein proximal translation of the insertion instrument while attached to the intradiscal shield is configured to seat the one or more anchors of the intradiscal shield into the spinal defect.

(B5) For the surgical system denoted as any of (B1) through (B4), the insertion instrument further comprising: a shield bore opening device received in the hollow tube of the shaft and configured to transition the bore of the intradiscal shield between the open configuration and the closed configuration, wherein the luer lock is configured to attach to a syringe, the syringe retaining a liquid comprising the protein crosslinker configured for spraying through the bore via the spraying end.

(B6) For the surgical system denoted as any of (B1) through (B5), wherein the distal tip comprises one or more extensions, wherein the one or more extensions are configured to engage the second side of the inner portion of the intradiscal shield to thereby stabilize a connection between the intradiscal shield and the insertion instrument.

(B7) For the surgical system denoted as any of (B1) through (B6), wherein the instrument engagement member comprises one or more stabilizers, wherein the one or more stabilizers are configured to stabilize the intradiscal shield.

(B8) For the surgical system denoted as any of (B1) through (B7), further comprising: an exterior shield having an attachment mechanism and configured to attach to an exterior wall of the spinal disc over the spinal defect, wherein the attachment mechanism is selected from a group consisting of: one or more sutures, one or more sutures coated with a degradable polymer containing a protein crosslinker, barbed tacks, one or more barbed tacks coated with a degradable polymer containing a protein crosslinker, and an adhesive material.

(B9) For the surgical system denoted as any of (B1) through (B8), the exterior shield further comprising: one or more sharp protrusions extending from the exterior shield, the one or more sharp protrusions configured to engage a vertebra juxtaposed to the spinal disc.

(C1) A method for providing structural integrity to a spinal disc having a spinal defect, the method comprising: attaching an intradiscal shield to a distal tip of an insertion instrument; inserting the intradiscal shield into the spinal defect, the intradiscal shield comprising: an outer barrier defining an inner portion and one or more anchors disposed in the outer barrier and extending outwardly therefrom, wherein the inner portion comprises a first side facing a central cavity of the spinal disc and a second side facing outwardly from the central cavity, wherein the inner portion defines a bore; seating the one or more anchors into a perimeter tissue of the spinal defect, the perimeter tissue defining the spinal defect; releasing a protein crosslinking reagent into the central cavity and the spinal defect, wherein the distal tip of the insertion instrument releases the protein crosslinking reagent through the bore of the intradiscal shield; and detaching the intradiscal shield from the distal tip.

(C2) The method denoted as (C1), further comprising: coating one or more of the outer barrier or the first side with the protein crosslinking reagent prior to inserting the intradiscal shield into the spinal defect.

(C3) The method denoted as (C1) or (C2), further comprising: rotating a shield bore opening device comprised in the insertion instrument to transition the bore from a closed configuration to an open configuration.

(C4) The method denoted as any of (C1) through (C3), further comprising: attaching an exterior shield to the spinal disc, wherein the exterior shield covers an exterior opening of the spinal defect.

(C5) The method denoted as any of (C1) through (C4), wherein attaching the exterior shield to the spinal disc comprises suturing the exterior shield to the spinal disc via a plurality of sutures, the plurality of sutures being coated in the protein crosslinking reagent.

Although the present disclosure has been described with reference to the embodiments illustrated in the attached drawing figures, it is noted that equivalents may be employed, and substitutions made herein without departing from the scope of the present disclosure as recited in the claims.

Having thus described various embodiments of the present disclosure, what is claimed as new and desired to be protected by Letters Patent includes the following:

1. An intradiscal shield configured to provide structural integrity to a spinal disc having a spinal defect, the intradiscal shield comprising:
   an outer barrier defining an inner portion,
      wherein the inner portion defines a bore,
         wherein the bore is configured to transition between an open configuration and a closed configuration,
         wherein, in the open configuration, the bore provides an opening for spraying a protein crosslinking reagent therethrough;
      a first side configured to face a central cavity of the spinal disc;
      a second side, opposite the first side, and configured to face outwardly from the central cavity,
         wherein the second side comprises an instrument engagement member,
         wherein the bore extends through the inner portion and the instrument engagement member,
         wherein the instrument engagement member comprises one or more stabilizers configured to stabilize the intradiscal shield; and
   one or more anchors extending from the outer barrier and angled acutely toward the second side,
      wherein distal translation of the intradiscal shield into the spinal defect bends the one or more anchors inwardly toward the outer barrier during insertion of the intradiscal shield into the spinal defect,
      wherein, when the intradiscal shield is inserted into the spinal defect, proximal biasing of the intradiscal shield inserts the one or more anchors into perimeter tissue of the spinal defect to maintain a position of the intradiscal shield within the spinal defect,
      wherein the one or more stabilizers extend through the inner portion and connect to the one or more anchors.

2. The intradiscal shield of claim 1,
wherein the bore biases into the closed configuration,
wherein the spinal defect is a surgical defect.

3. The intradiscal shield of claim 2,
wherein the bore is configured to transition into the open configuration upon interaction with an insertion instrument,
wherein, in the open configuration, the bore receives the protein crosslinking reagent to thereby release the protein crosslinking reagent into the central cavity of the spinal defect, such that the protein crosslinking reagent stabilizes the spinal disc.

4. The intradiscal shield of claim 1,
wherein one or more of the outer barrier or the first side comprise a coating of a degradable polymer having a protein crosslinker contained therein.

5. The intradiscal shield of claim 1, wherein the first side defines a first diameter, and the second side defines a second diameter greater than the first diameter.

6. The intradiscal shield of claim 5, wherein the first diameter is within a range of 0.5 millimeters to 6 millimeters.

7. The intradiscal shield of claim 1, wherein the one or more anchors include at least one of a ratchet-shaped edge, a projection, a clip, or a barbed pin.

8. A surgical system configured to insert an intradiscal shield into a spinal defect of a spinal disc, the surgical system comprising:
   the intradiscal shield, comprising:
      an outer barrier;
      an inner portion defined within the outer barrier, the inner portion having a first side configured to face inwardly within the spinal defect and a second side configured to face outwardly from the spinal defect;
one or more anchors disposed on the outer barrier and angled acutely toward the second side,
wherein distal translation of the intradiscal shield into the spinal defect bends the one or more anchors inwardly toward the outer barrier during insertion of the intradiscal shield into the spinal defect,
wherein, when the intradiscal shield is inserted into the spinal defect, proximal biasing of the intradiscal shield inserts the one or more anchors into perimeter tissue of the spinal defect to maintain a position of the intradiscal shield within the spinal defect;
an instrument engagement member disposed on the second side,
wherein the instrument engagement member comprises one or more stabilizers configured to stabilize the intradiscal shield,
wherein the one or more stabilizers extend through the inner portion and connect to the one or more anchors; and
a bore defined by the inner portion and the instrument engagement member, the bore configured to transition between an open configuration and a closed configuration; and
an insertion instrument, comprising:
a luer lock disposed at a proximal end;
a shaft extending distally from the luer lock and defining a hollow tube therein;
a distal tip configured to transiently attach to the instrument engagement member of the intradiscal shield; and
a spraying end comprised in the distal tip,
wherein the bore of the intradiscal shield is configured to receive the spraying end of the insertion instrument to thereby maintain the bore in the open configuration,
wherein the spraying end sprays a protein crosslinker through the bore when the bore is in the open configuration.

9. The surgical system of claim 8,
wherein the spraying end sprays the protein crosslinker through the bore into the spinal defect when the bore is in the open configuration, to thereby stabilize the spinal disc having the spinal defect.

10. The surgical system of claim 8,
wherein the bore of the intradiscal shield biases into the closed configuration.

11. The surgical system of claim 8,
wherein proximal translation of the insertion instrument while attached to the intradiscal shield is configured to seat the one or more anchors of the intradiscal shield into the spinal defect.

12. The surgical system of claim 11, the insertion instrument further comprising:
a shield bore opening device received in the hollow tube of the shaft and configured to transition the bore of the intradiscal shield between the open configuration and the closed configuration,
wherein the luer lock is configured to attach to a syringe, the syringe retaining a liquid comprising the protein crosslinker configured for spraying through the bore via the spraying end.

13. The surgical system of claim 8,
wherein the distal tip comprises one or more extensions,
wherein the one or more extensions are configured to engage the second side of the inner portion of the intradiscal shield to thereby stabilize a connection between the intradiscal shield and the insertion instrument.

14. The surgical system of claim 8, further comprising:
an exterior shield having an attachment mechanism and configured to attach to an exterior wall of the spinal disc over the spinal defect,
wherein the attachment mechanism is selected from a group consisting of: one or more sutures, one or more sutures coated with a degradable polymer containing a protein crosslinker, barbed tacks, one or more barbed tacks coated with a degradable polymer containing a protein crosslinker, and an adhesive material.

15. The surgical system of claim 14, the exterior shield further comprising:
one or more sharp protrusions extending from the exterior shield, the one or more sharp protrusions configured to engage a vertebra juxtaposed to the spinal disc.

16. A method for providing structural integrity to a spinal disc having a spinal defect, the method comprising:
attaching an intradiscal shield to a distal tip of an insertion instrument;
inserting the intradiscal shield into the spinal defect, the intradiscal shield comprising:
an outer barrier defining an inner portion,
wherein the inner portion comprises a first side facing a central cavity of the spinal disc and a second side facing outwardly from the central cavity,
wherein the inner portion defines a bore;
one or more anchors disposed in the outer barrier and extending outwardly therefrom and angled acutely toward the second side,
wherein distal translation of the intradiscal shield into the spinal defect bends the one or more anchors inwardly toward the outer barrier during insertion of the intradiscal shield into the spinal defect; and
an instrument engagement member disposed on the second side,
wherein the bore extends through the inner portion and the instrument engagement member,
wherein the instrument engagement member comprises one or more stabilizers configured to stabilize the intradiscal shield,
wherein the one or more stabilizers extend through the inner portion and connect to the one or more anchors,
wherein the bore is configured to transition between an open configuration and a closed configuration;
seating the one or more anchors into a perimeter tissue of the spinal defect via proximal biasing of the intradiscal shield when the intradiscal shield is inserted into the spinal defect to maintain a position of the intradiscal shield within the spinal defect,
wherein the perimeter tissue defines the spinal defect;
releasing a protein crosslinking reagent into the central cavity and the spinal defect,
wherein the distal tip of the insertion instrument releases the protein crosslinking reagent through the bore of the intradiscal shield in the open configuration; and
detaching the intradiscal shield from the distal tip.

17. The method of claim 16, further comprising:
coating one or more of the outer barrier or the first side with the protein crosslinking reagent prior to inserting the intradiscal shield into the spinal defect.

18. The method of claim 16, further comprising:
rotating a shield bore opening device comprised in the insertion instrument to transition the bore from the closed configuration to the open configuration.

19. The method of claim 16, further comprising:
attaching an exterior shield to the spinal disc, wherein the exterior shield covers an exterior opening of the spinal defect.

20. The method of claim 19,
wherein attaching the exterior shield to the spinal disc comprises suturing the exterior shield to the spinal disc via a plurality of sutures, the plurality of sutures being coated in the protein crosslinking reagent.

* * * * *